US010138391B2

(12) United States Patent
Takao et al.

(10) Patent No.: US 10,138,391 B2
(45) Date of Patent: Nov. 27, 2018

(54) FLUORINATED COMPOUND, COMPOSITION FOR FORMING HARD COAT LAYER, AND ARTICLE HAVING HARD COAT LAYER

(71) Applicant: ASAHI GLASS COMPANY, LIMITED, Tokyo (JP)

(72) Inventors: Kiyotaka Takao, Tokyo (JP); Toyomichi Shimada, Tokyo (JP); Taiki Hoshino, Tokyo (JP)

(73) Assignee: AGC Inc., Tokyo (JP)

( * ) Notice: Subject to any disclaimer, the term of this patent is extended or adjusted under 35 U.S.C. 154(b) by 298 days.

(21) Appl. No.: 14/857,018

(22) Filed: Sep. 17, 2015

(65) Prior Publication Data

US 2016/0002488 A1    Jan. 7, 2016

Related U.S. Application Data

(63) Continuation of application No. PCT/JP2014/077506, filed on Oct. 16, 2014.

(30) Foreign Application Priority Data

Oct. 18, 2013 (JP) ................................. 2013-217742

(51) Int. Cl.
| | | |
|---|---|---|
| *C07D 251/30* | (2006.01) | |
| *C09D 135/02* | (2006.01) | |
| *C08G 65/00* | (2006.01) | |
| *C08G 18/02* | (2006.01) | |
| *C09D 4/00* | (2006.01) | |
| *C08F 290/06* | (2006.01) | |
| *C09D 171/00* | (2006.01) | |
| *C08J 7/04* | (2006.01) | |
| *C08G 65/332* | (2006.01) | |
| *C08G 65/333* | (2006.01) | |
| *C08L 71/00* | (2006.01) | |

(52) U.S. Cl.
CPC .......... *C09D 135/02* (2013.01); *C07D 251/30* (2013.01); *C08F 290/06* (2013.01); *C08G 65/007* (2013.01); *C08G 65/3324* (2013.01); *C08G 65/33348* (2013.01); *C08G 65/33355* (2013.01); *C08J 7/047* (2013.01); *C08L 71/00* (2013.01); *C09D 4/00* (2013.01); *C09D 171/00* (2013.01); *C08J 2367/02* (2013.01); *C08J 2433/06* (2013.01)

(58) Field of Classification Search
CPC ....... C07D 251/30; C08G 18/02; C08G 65/00
USPC .................................. 544/221, 222; 428/421
See application file for complete search history.

(56) References Cited

U.S. PATENT DOCUMENTS

| | | | |
|---|---|---|---|
| 5,973,089 A | 10/1999 | Meijs et al. | |
| 6,906,115 B2 * | 6/2005 | Hanazawa | ......... C08G 18/2885 428/421 |
| 2004/0181008 A1 | 9/2004 | Hanazawa et al. | |
| 2006/0069177 A1 | 3/2006 | Sachdev et al. | |
| 2008/0226923 A1 | 9/2008 | Kruse et al. | |
| 2011/0104467 A1 | 5/2011 | Wu et al. | |

FOREIGN PATENT DOCUMENTS

| | | |
|---|---|---|
| DE | 10 2005 042 899 A1 | 3/2007 |
| JP | 11-509562 | 8/1999 |
| JP | 2006-45159 | 2/2006 |
| JP | 2008-40262 | 2/2008 |
| JP | 4547642 | 9/2010 |
| JP | 4923572 | 4/2012 |
| WO | WO 03/002628 | 1/2003 |
| WO | WO 2004/044062 | 5/2004 |
| WO | WO 2009/133770 | 11/2009 |
| WO | WO 2013/121984 | 8/2013 |
| WO | WO 2013/121986 | 8/2013 |
| WO | WO 2014/136787 | 9/2014 |

OTHER PUBLICATIONS

JP 2008-40262, Feb. 21, 2008; Machine Translation Dec. 31, 2017.*
International Search Report dated Jan. 27, 2015 in PCT/JP2014/077506 filed Oct. 16, 2014.

* cited by examiner

*Primary Examiner* — Venkataraman Balasubramanian
(74) *Attorney, Agent, or Firm* — Oblon, McClelland, Maier & Neustadt, L.L.P.

(57) ABSTRACT

A fluorinated compound represented by $D^1$-$R^{f1}$—O—$CH_2$—$(C_mF_{2m}O)_n$-A (wherein $D^1$ is $CF_3$— or $CF_3$—O—, $R^{f1}$ is a $C_{1-20}$ fluoroalkylene group containing at least one hydrogen atom, a $C_{2-20}$ fluoroalkylene group containing at least one hydrogen atom and having an etheric oxygen atom between carbon-carbon atoms, etc., m is an integer of from 1 to 6, n is an integer of from 1 to 200, and A is a monovalent organic group having at least one (meth)acryloyl group), which is capable of imparting excellent antifouling properties (oily ink repellency, fingerprint stain removability) and lubricity to e.g. a hard coat layer; a hard coat layer-forming composition which contains such a fluorinated compound; and an article having a hard coat layer formed from such a composition.

13 Claims, No Drawings

FLUORINATED COMPOUND, COMPOSITION FOR FORMING HARD COAT LAYER, AND ARTICLE HAVING HARD COAT LAYER

This application is a continuation of PCT Application No. PCT/JP2014/077506 filed on Oct. 16, 2014, which is based upon and claims the benefit of priority from Japanese Patent Application No. 2013-217742 filed on Oct. 18, 2013. The contents of those applications are incorporated herein by reference in their entireties.

TECHNICAL FIELD

The present invention relates to a fluorine compound, a hard coat layer-forming composition containing such a fluorine compound, and an article having a hard coat layer formed from such a composition.

BACKGROUND ART

Optical articles, displays, optical recording media, etc. are usually provided, on their surface, with a hard coat layer to prevent scratching, etc.

Further, such articles are desired to have properties whereby fouling (such as fingerprints, sebum, sweat, cosmetics, foods, oily ink, etc.) is less likely to attach on their surface, or fouling, if has attached on their surface, can easily be removed, i.e. antifouling properties. For example, if fouling attaches on the surface of an eyeglass lens, good visibility tends to be impaired and visual quality tends to be deteriorated. If fouling attaches on the surface of an optical recording medium, a trouble is likely to be caused in recording or reproducing a signal. If fouling attaches on the surface of a display, the visibility tends to be low, and in the case of a display provided with a touch panel, the operation efficiency tends to be adversely affected.

As materials capable of imparting antifouling properties to a hard coat layer, the following ones have been proposed.

(1) A fluorinated polymer having, in its main chain, a poly(oxyperfluoroalkylene) chain (Patent Document 1).

(2) A water/oil repellent having such a structure that it has a perfluoromethyl group at its molecular terminal, and an oxyperfluoroalkylene group is bonded to the perfluoromethyl group (Patent Document 2).

PRIOR ART DOCUMENTS

Patent Documents

Patent Document 1: Japanese Patent No. 4,547,642
Patent Document 2: Japanese Patent No. 4,923,572

DISCLOSURE OF INVENTION

Technical Problem

However, according to a finding by the present inventors, the hard coat layer employing the fluorinated polymer of (1) is inadequate in antifouling properties. Further, its lubricity is also inadequate.

On the other hand, the hard coat layer employing the water/oil repellent of (2) is excellent in antifouling properties, but the hard coat layer is inadequate in lubricity. If such a hard coat layer having inadequate lubricity is provided on the surface of e.g. a display provided with a touch panel, the sense of touch to the touch panel tends to be poor and the operation efficiency tends to be low.

It is an object of the present invention to provide a fluorinated compound capable of imparting excellent antifouling properties (oily ink repellency, fingerprint stain removability) and lubricity to an object (such as a hard coat layer), a hard coat layer-forming composition capable of forming a hard coat layer excellent in antifouling properties and lubricity, and an article having a hard coat layer excellent in antifouling properties and lubricity.

Solution to Problem

The present invention provides a fluorinated compound, a hard coat layer-forming composition, and an article having a hard coat layer, which have the following constructions [1] to [14].

[1] A fluorinated compound represented by the following formula (1):

$$D^1\text{-}R^{f1}\text{—}O\text{—}CH_2\text{—}(C_mF_{2m}O)_n\text{-}A \tag{1}$$

wherein $D^1$ is $CF_3$— or $CF_3$—O—, $R^{f1}$ is a $C_{1\text{-}20}$ fluoroalkylene group containing at least one hydrogen atom, a $C_{2\text{-}20}$ fluoroalkylene group containing at least one hydrogen atom and having an etheric oxygen atom between carbon-carbon atoms, a $C_{1\text{-}20}$ alkylene group, or a $C_{2\text{-}20}$ alkylene group having an etheric oxygen atom between carbon-carbon atoms, m is an integer of from 1 to 6, n is an integer of from 1 to 200, provided that when n is at least 2, $(C_mF_{2m}O)_n$ may be one composed of at least 2 types of $C_mF_{2m}O$ different in m, and A is a monovalent organic group having at least one —C(=O)—CR$^1$=CH$_2$ (wherein R$^1$ is a hydrogen atom or a methyl group).

[2] The fluorinated compound according to [1], wherein said $(C_mF_{2m}O)_n$ is $\{(CF_2O)_{n1}(CF_2CF_2O)_{n2}\}$ (wherein n1 is an integer of at least 1, and n2 is an integer of at least 0, provided that n1+n2 is an integer of from 1 to 200, and bonding order of n1 number of $CF_2O$ and n2 number of $CF_2CF_2O$ is not limited).

[3] The fluorinated compound according to [1] or [2], wherein said $R^{f1}$ is represented by the following formula (2-1), a group represented by the following formula (2-2), or a group represented by the following formula (2-3):

$$-R^F\text{—}O\text{—}CHFCF_2\text{—} \tag{2-1}$$

$$-R^F\text{—}CHFCF_2\text{—} \tag{2-2}$$

$$-R^F\text{—}C_zH_{2z} \tag{2-3}$$

wherein $R^F$ is a single bond, a $C_{1\text{-}5}$ perfluoroalkylene group, or a $C_{2\text{-}15}$ perfluoroalkylene group having an etheric oxygen atom between carbon-carbon atoms, and z is an integer of from 1 to 4.

[4] The fluorinated compound according to any one of [1] to [3], wherein said A is represented by the following formula (A1):

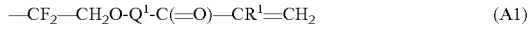
$$-CF_2\text{—}CH_2O\text{-}Q^1\text{-}C(=O)\text{—}CR^1=CH_2 \tag{A1}$$

wherein $Q^1$ is a $C_{1\text{-}100}$ bivalent organic group having no fluorine atom, and $R^1$ is a hydrogen atom or $CH_3$.

[5] The fluorinated compound according to [4], wherein said $Q^1$ has at least one type of a group represented by the following formula (3), a group represented by the following formula (4), or a group represented by the following formula (5):

$$-(CH_2CH_2O)_p\text{—} \tag{3}$$

$$-(CH_2CH(CH_3)O)_q\text{—} \tag{4}$$

$$-\{C(=O)C_tH_{2t}O\}_k\text{—} \tag{5}$$

where each of p, q, k and t is an integer of from 1 to 20.

[6] The fluorinated compound according to [5], wherein said $Q^1$ is a group represented by the following formula (6):

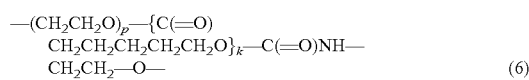

where each of p and k is an integer of from 1 to 10.

[7] The fluorinated compound according to any one of [1] to [3], wherein said A is represented by the following formula (A2):

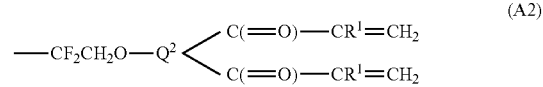

wherein $Q^2$ is a trivalent organic group, and each of two $R^1$, which are independent of each other, is a hydrogen atom or $CH_3$.

[8] The fluorinated compound according to [7], wherein said $Q^2$ has any of groups represented by the following formulae (7-1) to (7-6):

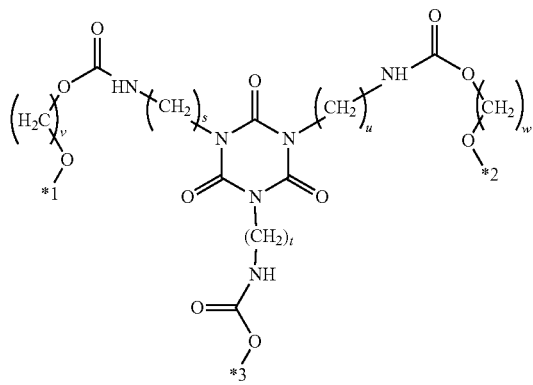

(7-1)

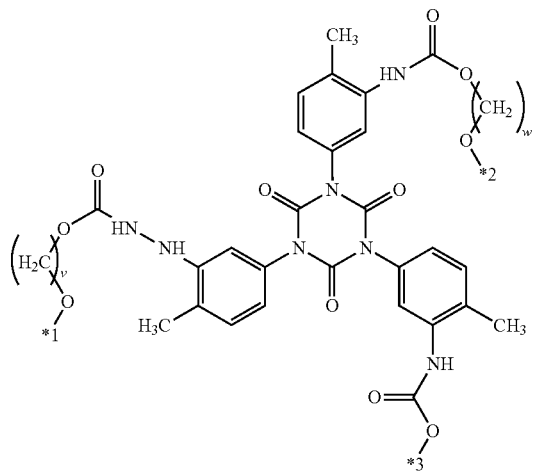

(7-2)

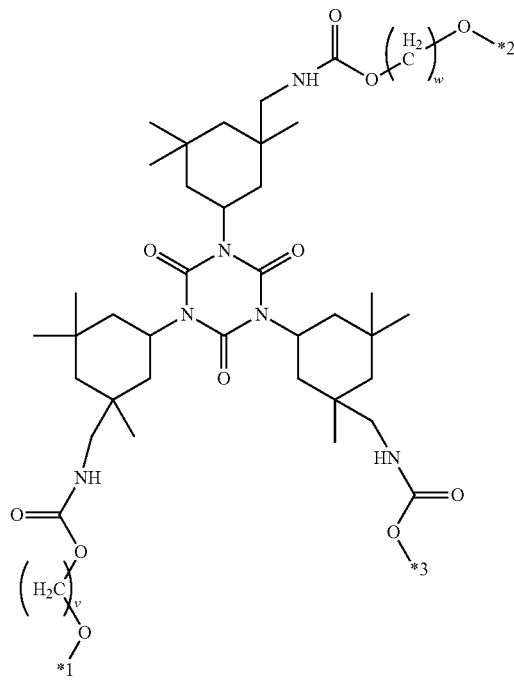

(7-3)

(7-4)

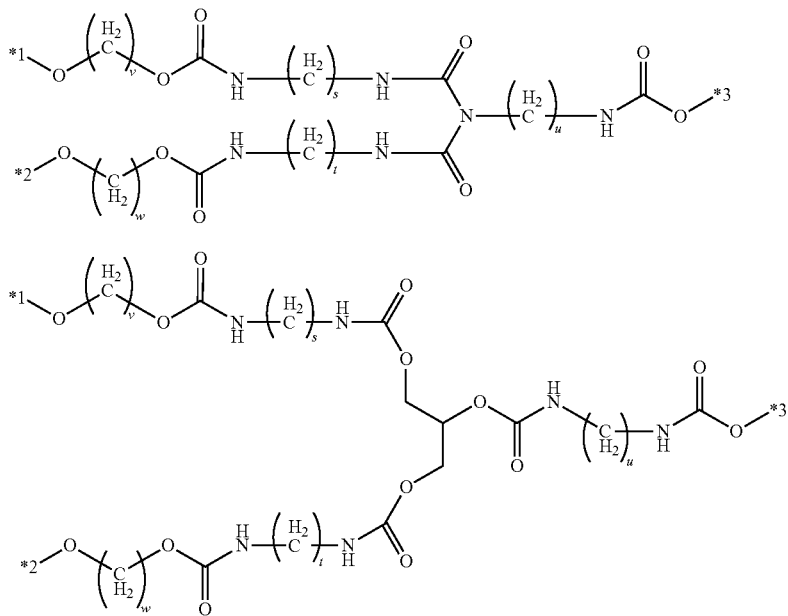

(7-5)

(7-6)

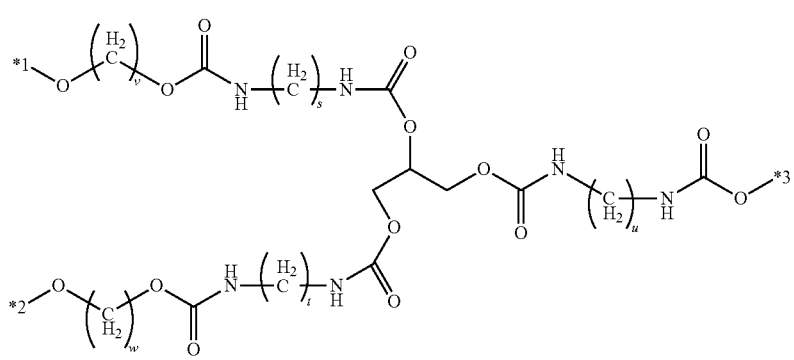

wherein each of s, t, u, v and w which are independent of one another, is an integer of from 2 to 10, and *1, *2 and *3 are terminals which are bonded to other groups, i.e. each of *1 and *2 is bonded to $-C(=O)-CR^1=CH_2$ in the above formula (A2), and *3 is bonded to $(C_mF_{2m}O)_n$ in the above formula (1) via $-CH_2CF_2-$ or a bivalent organic group having $-CH_2CF_2-$ at its one terminal.

[9] The fluorinated compound according to any one of [1] to [8], which has a number average molecular weight of from 800 to 80,000.

[10] A hard coat layer-forming composition comprising a fluorinated compound as defined in any one of [1] to [9], a photopolymerizable compound (excluding the above fluorinated compound), and a photopolymerization initiator.

[11] The hard coat layer-forming composition according to [10], which further contains a liquid medium.

[12] The hard coat layer-forming composition according to [11], wherein the content of the fluorinated compound is from 0.01 to 5 mass % in the solid content (100 mass %).

[13] An article comprising a substrate and a hard coat layer formed from the hard coat layer-forming composition as defined in any one of [10] to [12].

[14] The article according to [13], wherein the material for the substrate is a metal, a resin, a glass, a ceramics, or a composite material thereof.

Advantageous Effects of Invention

The fluorinated compound of the present invention is capable of imparting excellent antifouling properties and lubricity to an object. Further, in addition, the fluorinated compound of the present invention is excellent also in compatibility with other components.

The hard coat layer-forming composition of the present invention is capable of forming a hard coat layer excellent in antifouling properties and lubricity. Further, in addition, the hard coat layer-forming composition of the present invention is excellent also in storage stability.

The article of the present invention has a hard coat layer excellent in antifouling properties and lubricity.

DESCRIPTION OF EMBODIMENTS

In this specification, a compound represented by the formula (1) will be referred to as compound (1). Compounds represented by other formulae will also be referred to in the same manner.

The following definitions of terms will be applied to the entire specification including the claims.

An "etheric oxygen atom" means an oxygen atom to form an ether bond ($-O-$) between carbon-carbon atoms.

A "fluoroalkylene group" means a group having some or all of hydrogen atoms in an alkylene group substituted by fluorine atoms, and a "perfluoroalkylene group" means a group having all of hydrogen atoms in an alkylene group substituted by fluorine atoms. A "perfluoroalkyl group" means a group having all of hydrogen atoms in an alkyl group substituted by fluorine atoms.

An "oxyperfluoroalkylene group" means a group having an oxygen atom at one terminal of a perfluoroalkylene group, and its chemical formula shall be presented so that the oxygen atom is disposed on the right hand side of the perfluoroalkylene group.

A group represented by —C(=O)—CR$^1$=CH$_2$ (wherein R$^1$ is a hydrogen atom or a methyl group) will be hereinafter referred to as a "(meth)acryloyl group". The (meth)acryloyl group is a general term for an acryloyl group and a methacryloyl group.

A compound represented by HO—C(=O)—CR$^1$=CH$_2$ will be hereinafter referred to as "(meth)acrylic acid", and an ester of (meth)acrylic acid will be referred to as a (meth)acrylate. The (meth)acrylate is a general term for an acrylate and a methacrylate.

An organic group is a group having carbon atoms.

[Fluorinated Compound]

The fluorinated compound of the present invention is compound (1) represented by the following formula (1):

$$D^1-R^{f1}-O-CH_2-(C_mF_{2m}O)_n-A \quad (1)$$

wherein D$^1$ is CF$_3$— or CF$_3$—O—, R$^{f1}$ is a C$_{1-20}$ fluoroalkylene group containing at least one hydrogen atom, a C$_{2-20}$ fluoroalkylene group containing at least one hydrogen atom and having an etheric oxygen atom between carbon-carbon atoms, a C$_{1-20}$ alkylene group, or a C$_{2-20}$ alkylene group having an etheric oxygen atom between carbon-carbon atoms, m is an integer of from 1 to 6, n is an integer of from 1 to 200, provided that when n is at least 2, $(C_mF_{2m}O)_n$ may be one composed of at least 2 types of $C_mF_{2m}O$ different in m, and A is a monovalent organic group having at least one (meth)acryloyl group.

(Group D$^1$)

D$^1$ is CF$_3$— or CF$_3$—O—, and therefore, one terminal of compound (1) becomes CF$_3$—. Therefore, by using compound (1), it is possible to form a hard coat layer excellent in antifouling properties with a low surface energy.

$((C_mF_{2m}O)_n)$ $(C_mF_{2m}O)_n$ imparts antifouling properties and lubricity to a hard coat layer.

m is preferably an integer of from 1 to 3 with a view to sufficiently imparting antifouling properties and lubricity, more preferably 1 or 2 with a view to sufficiently imparting lubricity to a hard coat layer.

When m is at least 2, $C_mF_{2m}$ may be linear or branched, and is preferably linear with a view to sufficiently imparting antifouling properties and lubricity to a hard coat layer.

With a view to sufficiently imparting antifouling properties and lubricity to a hard coat layer, n is an integer of at least 2, more preferably an integer of at least 4, particularly preferably an integer of at least 5. From such a viewpoint that if the number average molecular weight of compound (1) is too large, the number of (meth)acryloyl groups in the after-mentioned group A present per unit molecular weight decreases, and the abrasion resistance of the hard coat layer lowers, and that the compatibility between compound (1) and other compounds in the hard coat layer-forming composition will be excellent, n is preferably an integer of at most 100, more preferably an integer of at most 80, particularly preferably an integer of at most 60.

When n is at least 2, $(C_mF_{2m}O)_n$ may be one composed of at least 2 types of $C_mF_{2m}O$ different in m.

In a case where at least 2 types of $C_mF_{2m}O$ different in m are present in $(C_mF_{2m}O)_n$, the bonding order of the respective plurality of $C_mF_{2m}O$ is not limited. For example, in a case where CF$_2$O and CF$_2$CF$_2$O are present, CF$_2$O and CF$_2$CF$_2$O may be randomly arranged, CF$_2$O and CF$_2$CF$_2$O may be alternately arranged, or a block composed of a plurality of CF$_2$O and a block composed of a plurality of CF$_2$CF$_2$O may be linked.

$(C_mF_{2m}O)_n$ is preferably $\{(CF_2O)_{n1}(CF_2CF_2O)_{n2}\}$ (wherein n1 is an integer of at least 1, and n2 is an integer of at least 0, provided that n1+n2 is an integer of from 1 to 200, and the bonding order of n1 number of CF$_2$O and n2 number of CF$_2$CF$_2$O is not limited) with a view to sufficiently imparting antifouling properties and lubricity to a hard coat layer.

$\{(CF_2O)_{n1}(CF_2CF_2O)_{n2}\}$ is excellent in motility, whereby the hard coat layer will be excellent in lubricity. Particularly, $(CF_2O)_{n1}$ is a group having one carbon atom and an oxygen atom, and thus is particularly excellent in motility.

$\{(CF_2O)_{n1}(CF_2CF_2O)_{n2}\}$ is preferably such that the terminal on the side bonded to —CH$_2$—, of $\{(CF_2O)_{n1}(CF_2CF_2O)_{n2}\}$, is CF$_2$O, whereby the production of compound (1) will be easy. $\{(CF_2O)_{n1}(CF_2CF_2O)_{n2}\}$ wherein the terminal on the side bonded to —CH$_2$— is CF$_2$O, will be hereinafter represented by $CF_2O\{(CF_2O)_{n1-1}(CF_2CF_2O)_{n2}\}$. Here, also in $CF_2O\{(CF_2O)_{n1-1}(CF_2CF_2O)_{n2}\}$, the bonding order of (n1–1) number of (CF$_2$O) and n2 number of (CF$_2$CF$_2$O) is not limited, as mentioned above.

n1 is an integer of at least 1. With a view to sufficiently imparting antifouling properties and lubricity to a hard coat layer, n1 is preferably an integer of at least 2, particularly preferably an integer of at least 3. From such a view point that if the number average molecular weight of compound (1) is too large, the number of (meth)acryloyl groups in the after-mentioned group A present per unit molecular weight decreases, and the abrasion resistance of the hard coat layer lowers, and that the compatibility between compound (1) and other components in the hard coat layer-forming composition will be excellent, n1 is preferably an integer of at most 50, more preferably an integer of at most 40, particularly preferably an integer of at most 30.

n2 is an integer of at least 0. With a view to sufficiently imparting antifouling properties and lubricity to a hard coat layer, n2 is preferably an integer of at least 1, particularly preferably an integer of at least 2. From such a view point that if the number average molecular weight of compound (1) is too large, the number of (meth)acryloyl groups in the after-mentioned group A present per unit molecular weight decreases, and the abrasion resistance of the hard coat layer lowers, and that the compatibility between compound (1) and other components in the hard coat layer-forming composition will be excellent, n2 is preferably an integer of at most 50, more preferably an integer of at most 40, particularly preferably an integer of at most 30.

With respect to the ratio of n1 and n2, n2 is preferably from 0 to 3 times n1, with a view to sufficiently imparting lubricity to a hard coat layer.

Compound (1) may be produced as a mixture of a plurality of compounds different in the number of n in $(C_mF_{2m}O)_n$. In such a case, the average value of n as the mixture is preferably from 2 to 100, particularly preferably from 4 to 80. Further, compound (1) may be produced as a mixture of a plurality of compounds different in the numbers of n1 and n2 in $\{(CF_2O)_{n1}(CF_2CF_2O)_{n2}\}$. In such a case, as the mixture, the average value of n1 is preferably from 1 to 50, and the average value of n2 is preferably from 1 to 50.

(Group $R^{f1}$)

The number of hydrogen atoms in $R^{f1}$ is preferably at least 1, whereby the lubricity of a hard coat layer will be sufficiently good. The number of hydrogen atoms in $R^{f1}$ is preferably at most (the number of carbon atoms in $R^{f1}$)×2, more preferably at most (the number of carbon atoms in $R^{f1}$), whereby the lubricity of a hard coat layer will be sufficiently good.

As $R^{f1}$ has hydrogen atom(s), the above-mentioned motility of $(C_mF_{2m}O)_n$ will be further improved, the lubricity of the hard coat layer will be sufficiently good, and the compatibility of compound (1) and other components in the hard coat layer-forming composition will be excellent. On the other hand, if $R^{f1}$ has no hydrogen atom, the lubricity of the hard coat layer will be inadequate, the compatibility of compound (1) and other components in the hard coat layer-forming composition will be inadequate, and the storage stability of the hard coat layer-forming composition will be inadequate.

From the viewpoint of the production efficiency of compound (1), $R^{f1}$ is preferably a group represented by the following formula (2-1), a group represented by the following formula (2-2), or a group represented by the following formula (2-3). Here, $R^F$ is a group to be bonded to $D^1$.

$$—R^F—O—CHFCF_2— \quad (2\text{-}1)$$

$$—R^F—CHFCF_2— \quad (2\text{-}2)$$

$$—R^F—C_zH_{2z}— \quad (2\text{-}3)$$

wherein $R^F$ is a single bond, a $C_{1-15}$ perfluoroalkylene group, or a $C_{2-15}$ perfluoroalkylene group having an etheric oxygen atom between carbon-carbon atoms, and z is an integer of from 1 to 4.

With a view to sufficiently imparting antifouling properties and lubricity to a hard coat layer, $R^F$ is preferably a $C_{1-9}$ perfluoroalkylene group, or a $C_{2-13}$ perfluoroalkylene group having an etheric oxygen atom between carbon-carbon atoms. The perfluoroalkylene group may be linear or branched.

z is preferably an integer of from 1 to 3. When z is at least 3, $C_zH_{2z}$ may be linear or branched, and is preferably linear.

When $R^{f1}$ is represented by the formula (2-1), the following groups may be mentioned as specific examples of group $D^1$-$R^{f1}$—.

$CF_3$—O—$CHFCF_2$—,
$CF_3$—$CF_2$—O—$CHFCF_2$—,
$CF_3$—$CF_2CF_2$—O—$CHFCF_2$—,
$CF_3$—$CF_2CF_2CF_2$—O—$CHFCF_2$—,
$CF_3$—$CF_2CF_2CF_2CF_2CF_2$—O—$CHFCF_2$—,
$CF_3$—O—$CF_2CF_2$—O—$CHFCF_2$—,
$CF_3$—$CF_2OCF_2CF_2$—O—$CHFCF_2$—,
$CF_3$—O—$CF_2CF_2OCF_2CF_2$—O—$CHFCF_2$—,
$CF_3$—$CF_2OCF_2CF_2OCF_2CF_2$—O—$CHFCF_2$—,
$CF_3$—$CF_2CF_2OCF(CF_3)CF_2$—O—$CHFCF_2$—,
$CF_3$—$CF_2CF_2OCF(CF_3)CF_2OCF(CF_3)CF_2$—O—$CHFCF_2$—.

When $R^{f1}$ is represented by the formula (2-2), the following groups may be mentioned as specific examples of group $D^1$-$R^{f1}$—.

$CF_3$—$CHFCF_2$—,
$CF_3$—$CF_2$—$CHFCF_2$—,
$CF_3$—$CF_2CF_2$—$CHFCF_2$—,
$CF_3$—$CF_2CF_2CF_2$—$CHFCF_2$—.

When $R^{f1}$ is represented by the formula (2-3), the following groups may be mentioned as specific examples of group $D^1$-$R^{f1}$—.

$CF_3$—$CH_2$—,
$CF_3$—$CF_2$—$CH_2$—,
$CF_3$—$CF_2CF_2$—$CH_2$—,
$CF_3$—$CF_2CF_2CF_2$—$CH_2$—,
$CF_3$—$CF_2CF_2CF_2CF_2$—$CH_2$—,
$CF_3$—$CF_2CF_2CF_2CF_2CF_2$—$CH_2$—,
$CF_3$—$CF_2CF_2CF_2CF_2CF_2CF_2$—$CH_2$—,
$CF_3$—$CH_2CH_2$—,
$CF_3$—$CF_2$—$CH_2CH_2$—,
$CF_3$—$CF_2CF_2$—$CH_2CH_2$—,
$CF_3$—$CF_2CF_2CF_2$—$CH_2CH_2$—,
$CF_3$—$CF_2CF_2CF_2CF_2$—$CH_2CH_2$—,
$CF_3$—$CF_2CF_2CF_2CF_2CF_2$—$CH_2CH_2$—,
$CF_3$—$CF_2CF_2CF_2CF_2CF_2CF_2$—$CH_2CH_2$—,
$CF_3$—$CH_2CH_2CH_2$—,
$CF_3$—$CF_2$—$CH_2CH_2CH_2$—,
$CF_3$—$CF_2CF_2$—$CH_2CH_2CH_2$—,
$CF_3$—$CF_2CF_2CF_2$—$CH_2CH_2CH_2$—,
$CF_3$—$CF_2CF_2CF_2CF_2$—$CH_2CH_2CH_2$—,
$CF_3$—$CF_2CF_2CF_2CF_2CF_2$—$CH_2CH_2CH_2$—,
$CF_3$—$CF_2CF_2CF_2CF_2CF_2CF_2$—$CH_2CH_2CH_2$—,
$CF_3$—O—$CF_2$—$CH_2$—,
$CF_3$—$CF_2OCF_2$—$CH_2$—,
$CF_3$—O—$CF_2CF_2OCF_2$—$CH_2$—,
$CF_3$—$CF_2OCF_2CF_2OCF_2$—$CH_2$—,
$CF_3$—O—$CF_2CF_2OCF_2CF_2OCF_2$—$CH_2$—,
$CF_3$—$CF_2OCF_2CF_2OCF_2CF_2OCF_2$—$CH_2$—.

From the viewpoint of the production efficiency of compound (1), $R^{f1}$ is preferably a group represented by the formula (2-1), and group $D^1$-$R^{f1}$— is particularly preferably $CF_3$—$CF_2CF_2$—O—$CHFCF_2$— or $CF_3$—$CF_2CF_2CF_2CF_2CF_2$—O—$CHFCF_2$—.

A compound represented by the following formula (8) is preferred as a starting compound for introducing group A into $D^1$-$R^{f1}$—O—$CH_2$—$(C_mF_{2m}O)_n$—.

$$D^1\text{-}R^{f1}—O—CH_2—(C_mF_{2m}O)_n—R^2—Y \quad (8)$$

In this formula, $R^2$ is a single bond or a bivalent organic group which may have fluorine atoms, and Y is a reactive group. $R^2$ is preferably an alkylene group, or a fluoroalkylene group having a methylene group at its Y side terminal, which has at most 10 carbon atoms. Y may, for example, be a hydroxy group, a carboxy group, an epoxy group or an amino group, particularly preferably a hydroxy group. —$R^2$—Y is preferably —$CF_2CH_2OH$.

The above starting compound is preferably a compound represented by the following formula (8-1) such as the after-described compound (α2).

$$D^1\text{-}R^{f1}—O—CH_2—(C_mF_{2m}O)_n—CF_2CH_2OH \quad (8\text{-}1)$$

Compound (8-1) is a monool, and by utilizing the reactivity of its hydroxy group, a (meth)acryloyl group is introduced to produce compound (1).

Compound (8-1) may be obtained, for example, by a method of reacting a fluorinated olefin having D1 and one molecule of a fluorinated diol having hydroxy group-containing organic groups at both terminals of $(C_mF_{2m}O)_n$ so that one hydroxy group of the fluorinated diol is added to an unsaturated group of the fluorinated olefin. As the fluorinated diol, a commercially available fluorinated diol may be used. As the fluorinated diol, the after-described compound (α1) may, for example, be mentioned.

(Group A)

Group A is a monovalent organic group having at least one (meth)acryloyl group. As group A has (meth)acryloyl group(s), compound (1) will, under light irradiation, react with a photopolymerizable compound contained in the hard coat layer-forming composition, to impart excellent abrasion resistance to the hard coat layer. A photocurable hard coat layer-forming composition requires no heating at the time of curing and thus is useful for forming a hard coat layer on a substrate made of a resin having a relatively low heat resistance as compared with glass, etc.

The number of (meth)acryloyl groups in group A is preferably from 1 to 3, particularly preferably 1 or 2.

Group A includes a group to be formed by a reaction of Y of $-R^2-Y$ in compound (8). In a case where $-R^2-Y$ is $-CF_2CH_2OH$, group A has $-CF_2CH_2O-$ at its terminal, and $CF_2$ of $-CF_2CH_2O-$ is bonded to a terminal oxygen atom of $(C_mF_{2m}O)_n$.

As group A, groups represented by the following formulae (A1) to (A3) may be mentioned. $-CF_2CH_2O-$ in the following formulae (A1) to (A3) is a group having a hydrogen atom of a hydroxy group excluded from the above $-CF_2CH_2OH$.

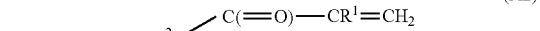

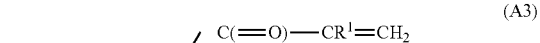

In the formulae (A1) to (A3), $Q^1$ is a bivalent organic group, $Q^2$ is a trivalent organic group, $Q^3$ is a tetravalent organic group, $R^1$ is a hydrogen atom or $CH_3$, and a plurality of $R^1$ in $Q^2$ and $Q^3$ may be the same or different.

The number of carbon atoms in each of $Q^1$ to $Q^3$ is preferably from 1 to 100, more preferably from 10 to 60. When the number of carbon atoms is at least the lower limit value in the above range, the compatibility of compound (1) and other components in the hard coat layer-forming composition will be excellent, and when it is at most the upper limit value in the above range, the antifouling properties of the hard coat layer will be better. $Q^1$ to $Q^3$ should better contain no fluorine atom. When $Q^1$ to $Q^3$ contain no fluorine atom, the compatibility of compound (1) and other components in the hard coat layer-forming composition will be excellent.

$Q^1$ to $Q^3$ may be linear or branched, and may have a ring structure. When they have a ring structure, the ring structure may be an aromatic ring or an aliphatic ring and is preferably an aliphatic ring.

$Q^1$ to $Q^3$ may have a hetero atom such as an oxygen atom, a sulfur atom or a nitrogen atom, and a group such as an ester group, an ether group (an etheric oxygen atom), a urethane group, a urea group, a carbonyl group, an imino group or a sulfonyl group. Further, each of $Q^1$ to $Q^3$ is preferably an organic group having no fluorine atom.

A group represented by the above formula (A1) (hereinafter referred to also as "group A1") is preferably such that $Q^1$ has at least one type of a group represented by the following formula (3), a group represented by the following formula (4), or a group represented by the following formula (5).

wherein each of p, q, k and t is an integer of from 1 to 20.

For example, p is preferably an integer of from 1 to 10, particularly preferably an integer of from 1 to 3. t is preferably an integer of from 1 to 8, and from the viewpoint of the production efficiency of compound (1), t is more preferably from 3 to 6, particularly preferably 5. k is preferably an integer of from 1 to 10, particularly preferably an integer of from 2 to 8.

For $Q^1$, it is preferred to add at least one molecule of an alkylene oxide or lactone to a hydroxy group of the above compound (8-1) to form a group represented by the above formula (3) to (5). Further, in order to adjust the reactivity of the hydroxy group, it is preferred to add ethylene carbonate to $-CF_2CH_2OH$ of the above compound (8-1) under decarboxylation to form $-CF_2CH_2OCH_2CH_2OH$, and then an alkylene oxide or lactone is reacted.

In a case where $Q^1$ has the group represented by the above formula (3), $Q^1$ may be introduced to compound (1), for example, by a method of adding at least one molecule of ethylene oxide or a method of reacting polyethylene glycol together with a bifunctional isocyanate compound. At the time of adding ethylene oxide, ethylene carbonate may be added under decarboxylation and then, ethylene oxide is added.

In a case where $Q^1$ has the group represented by the above formula (4), $Q^1$ may be introduced to compound (1), for example, by a method of adding at least one molecule of propylene oxide or a method of reacting polypropylene glycol together with a bifunctional isocyanate compound. At the time of adding propylene oxide, ethylene carbonate may be added under decarboxylation and then, propylene oxide is added.

In a case where $Q^1$ has the group represented by the above formula (5), $Q^1$ may be introduced to compound (1), for example, by a method of adding at least one molecule of lactone. At the time of adding at least one molecule of lactone, ethylene carbonate may be added under decarboxylation and then, lactone is added.

From the viewpoint of the production efficiency of compound (1), $Q^1$ preferably has at least a group represented by the formula (5) and more preferably is a group represented by the following formula (6).

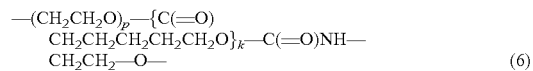

In the formula (6), p and k have the same meanings as p and k in the formula (3) and the formula (5).

Here, like compound (8-1), compounds having terminal hydroxy groups obtainable by introducing groups represented by the formulae (3) to (5) to compound (8-1) are monools each having a group represented by $D^1-R^{f1}-O-CH_2-(C_mF_{2m}O)_n-CF_2CH_2O-$. Such monools are preferred as starting materials for producing not only compound (1) having $Q^1$, but also compound (1) having $Q^2$ and compound (1) having $Q^3$.

As a group represented by the above formula (A2) (hereinafter referred to also as "group A2"), a group may be mentioned wherein $-CF_2CH_2O-Q^2<$ has any of groups represented by the following formulae (7-1) to (7-6). A compound having such a group can be obtained by reacting a monool having a group represented by D¹-R^f¹—O—CH₂—(C_mF_{2m}O)_n—CF₂CH₂O—, a hydroxyalkyl(meth)acrylate and a triisocyanate compound.
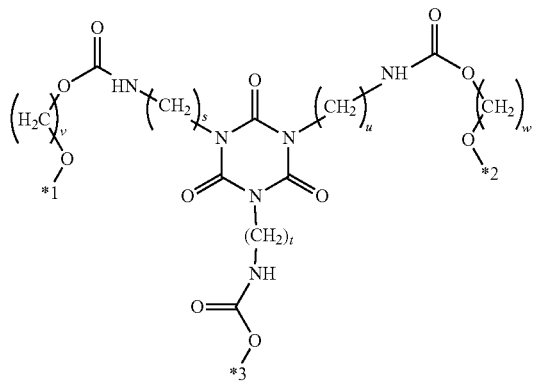
(7-1)
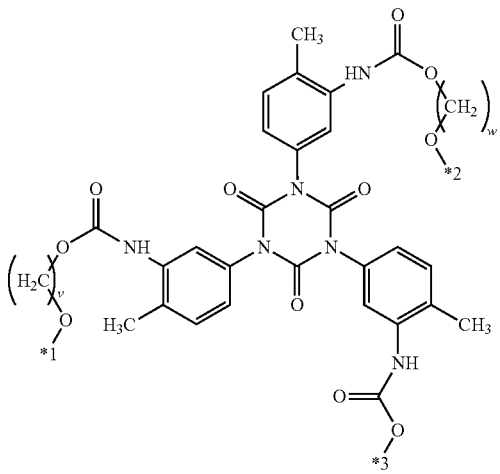
(7-2)
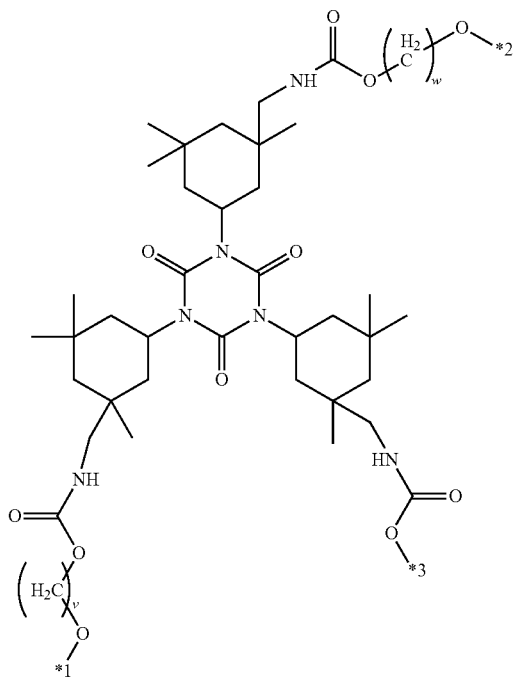
(7-3)
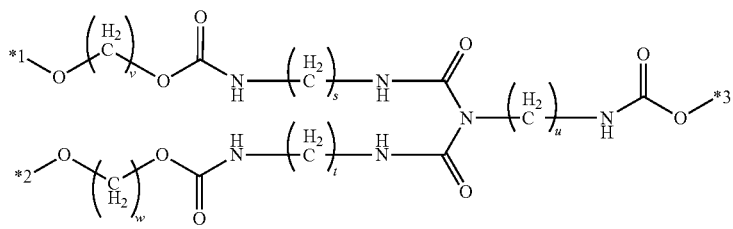
(7-4)

(7-5)

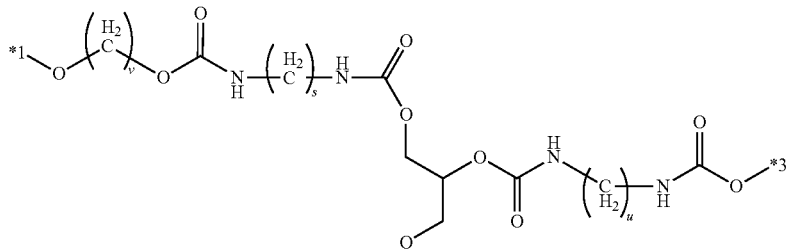

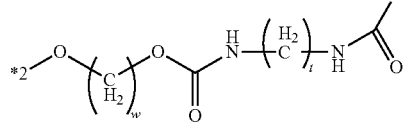

(7-6)

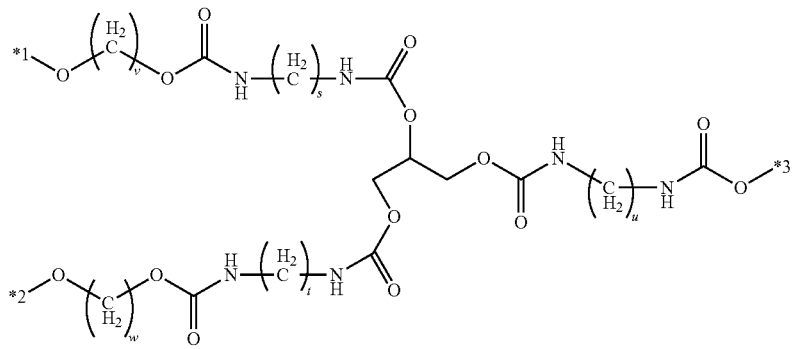

In the formulae (7-1) to (7-6), each of s, t, u, v and w which are independent of one another, is an integer of from 2 to 10. *1, *2 and *3 are terminals which are bonded to other groups, and it is preferred that each of *1 and *2 is bonded to $—C(=O)—CR^1=CH_2$ in the formula (A2), and *3 is bonded to $(C_mF_{2m}O)_n$ in the formula (1) via $—CH_2CF_2—$ or a bivalent organic group having $—CH_2CF_2—$ at its one terminal. The bivalent organic group having $—CH_2CF_2—$ at its one terminal may, for example, be a $C_{1-10}$ alkylene group having $—CH_2CF_2—$ at its one terminal, or a bivalent group represented by any of the above formulae (2) to (6), having $—CH_2CF_2—$ at its one terminal, provided that the $CF_2$ side of $—CH_2CF_2—$ is to be bonded to $(C_mF_{2m}O)_n$.

Compound (1) having a group represented by the above formula (A3) can be obtained by using a tetraisocyanate compound instead of the triisocyanate compound in the above synthesis of compound (1) having the above group (A2).

(Preferred Embodiments of Compound (1))

As compound (1), compounds represented by the following formulae (111), (112), (121), (122), (131) and (132) are preferred. Further, compounds represented by the following formulae (14-1) to (14-6) are preferred. Among them, particularly preferred as compound (1) are compounds represented by the following formulae (111), (112), (121), (122), (131), (132) and (14-1).

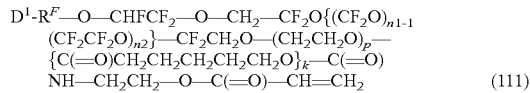

(111)

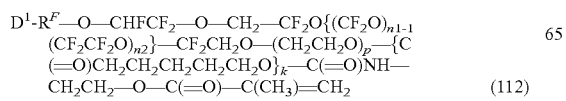

(112)

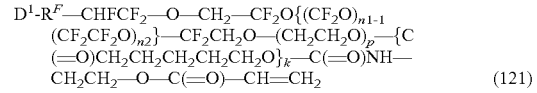

(121)

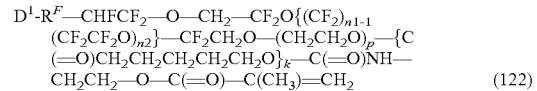

(122)

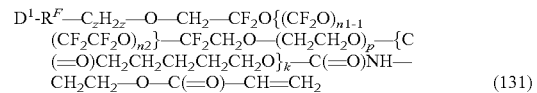

(131)

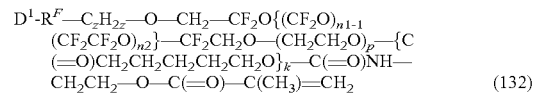

(132)

(14-1)

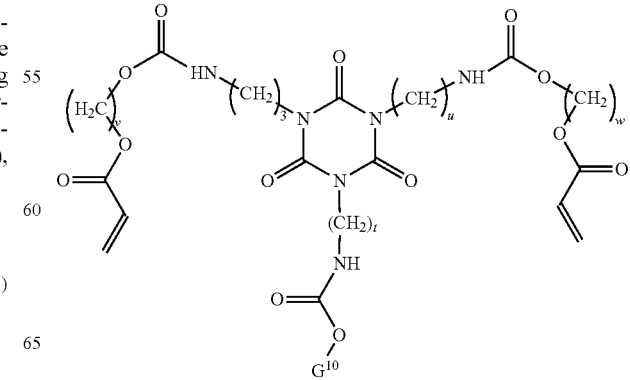

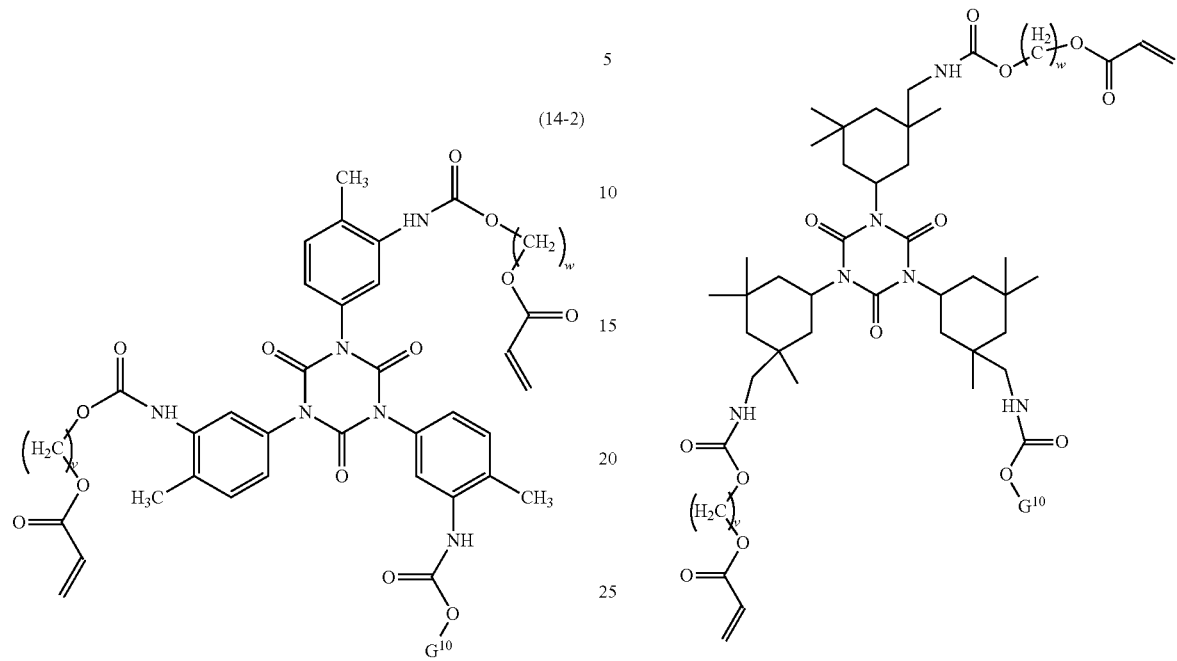
In the formulae (14-1) to (14-3), $G^{10}$ is $D^1$-$R^{f1}$—O—$CH_2CF_2O\{(CF_2O)_{n1-1}(CF_2CF_2O)_{n2}\}CF_2CH_2$—. s, t, u, v and w have the same meanings as in the formulae (7-1) to (7-3), and their preferred ranges are also the same.
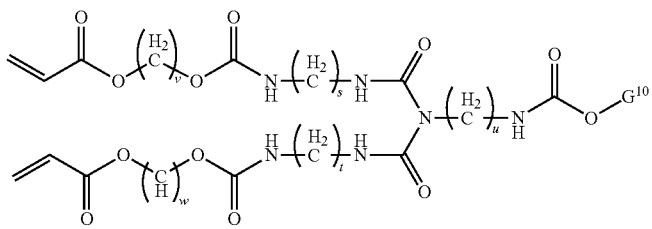
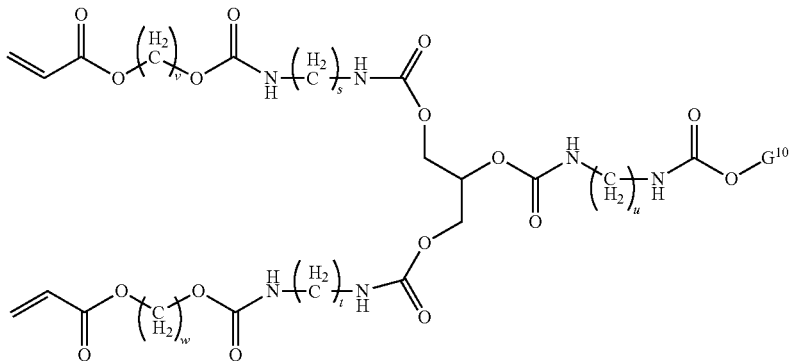

(14-6)

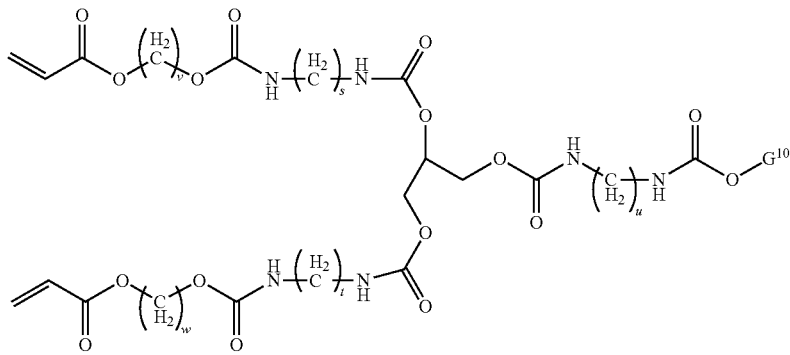

In the formulae (14-4) to (14-6), $G^{10}$ is $D^1$-$R^{f1}$—O—$CH_2CF_2O\{(CF_2O)_{n1-1}(CF_2CF_2O)_{n2}\}CF_2CH_2$—. s, t, u, v and w have the same meanings as in the formulae (7-1) to (7-3), and their preferred ranges are also the same.

As compound (1), particularly preferred is a compound of the following formula (111-1) wherein group $D^1$-$R^{f1}$— is $CF_3$—$CF_2CF_2$—O—$CHFCF_2$—, p is 1, and k is 2.

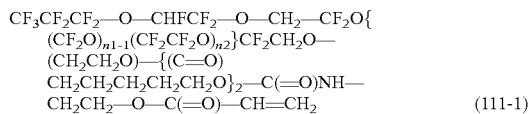  (111-1)

(Proportion of Fluorine Atoms and Number Average Molecular Weight)

The proportion of fluorine atoms in compound (1) (100 mass %) is preferably from 0.1 to 80 mass %, more preferably from 1 to 70 mass %, particularly preferably from 5 to 65 mass %.

Further, from the viewpoint of improving the antifouling properties of a hard coat layer, among fluorine atoms (100 mass %) in compound (1), from 40 to 100 mass % is preferably fluorine atoms in $(C_mF_{2m}O)_n$, and from 50 to 100 mass % is more preferably fluorine atoms in $(C_mF_{2m}O)_n$.

When the proportion of fluorine atoms is within the above range, it is possible to impart excellent antifouling properties (oily ink repellency, fingerprint stain removability) and lubricity to a hard coat layer, and at the same time, compound (1) will be excellent in compatibility with other components in the hard coat layer-forming composition.

The proportion of fluorine atoms is measured by the method disclosed in Examples.

The number average molecular weight (Mn) of compound (1) is preferably from 800 to 80,000, more preferably from 1,000 to 40,000, particularly preferably from 1,200 to 30,000. When the number average molecular weight is within such a range, it is possible to impart excellent antifouling properties (oily ink repellency, fingerprint stain removability) and lubricity to a hard coat layer, and at the same time, compound (1) will be excellent in compatibility with other components in the hard coat layer-forming composition.

[Methods for Producing Fluorinated Compound]

Compound (1) can be produced by synthesizing the above-mentioned compound (8) as a starting compound, and then reacting compound (8) or its derivative, and a reactive compound having a (meth)acryloyl group. Or, it can be produced by bonding compound (8) or its derivative, and a reactive compound having a (meth)acryloyl group via a polyfunctional compound reactive with both compounds.

Hereinafter, the former method will be referred to as production method (i) and the latter method will be referred to as production method (ii).

As compound (8), the above-mentioned compound (8-1) is preferred. As a derivative of compound (8), a monool obtainable by introducing at least one type of groups represented by the above formulae (4) to (5) to the above compound (8-1) is preferred. Hereinafter, compound (8) and a derivative of compound (8), having one hydroxy group, will be generally referred to as a fluorinated monool.

Now, the production method (i) and the production method (ii) will be described wherein as an example of the starting compound, the above fluorinated monool is used.

Production method (i):

By reacting a fluorinated monool and a reactive compound having a (meth)acryloyl group and a reactive group reactive with a hydroxy group, it is possible to produce compound (1).

The reactive group of the reactive compound may, for example, be an isocyanate group, a halocarbonyl group, a carboxy group or an epoxy group. As the reactive group, an isocyanate group or a halocarbonyl group is preferred. As the reactive compound, a compound having one reactive group is preferred. The reactive compound has at least one (meth)acryloyl group, and the number of (meth)acryloyl groups is preferably from 1 to 4, more preferably 1. The reactive compound may, for example, be (meth)acryloyloxyethyl isocyanate or (meth)acrylic acid chloride.

Specifically, compound (1) can be produced, for example, by reacting acrylic acid chloride and a fluorinated monool to convert the hydroxy group of the fluorinated monool to an acryloyloxy group. Or, compound (1) can be produced by reacting 2-acryloyloxyethyl isocyanate and a fluorinated monool to convert the hydroxy group of the fluorinated monool to —O—C(=O)NH—$CH_2CH_2$—O—C(=O)—CH=$CH_2$.

Production Method (ii):

By reacting a fluorinated monool and a reactive compound having a (meth)acryloyl group and a reactive group, via a polyfunctional compound having a functional group reactive with the reactive group and a functional group reactive with a hydroxy group, it is possible to produce compound (1). In this case, the reactive group of the reactive compound is preferably a hydroxy group, and as the polyfunctional compound, a compound having at least two functional groups reactive with hydroxy groups, is preferred. As the functional groups of the polyfunctional compound, isocyanate groups, halocarbonyl groups, carboxy groups, epoxy groups, etc. may be mentioned, and isocyanate groups are particularly preferred.

The reactive compound having a hydroxy group is a compound having at least one (meth)acryloyl group and at least one hydroxy group, and the number of hydroxy groups is preferably 1. The number of (meth)acryloyl groups is preferably from 1 to 8, more preferably from 1 to 4, particularly preferably 1. As the reactive compound having a hydroxy group, a hydroxyalkyl(meth)acrylate or a polyoxyalkylene glycol mono(meth)acrylate may, for example, be mentioned. Particularly, a hydroxyalkyl(meth)acrylate wherein the number of carbon atoms in the alkyl moiety is from 2 to 10, is preferred, and more preferred is a $C_{2-10}$ hydroxyalkyl acrylate having a linear hydroxyalkyl group which has a hydroxy group at its terminal.

The polyfunctional compound is preferably a polyisocyanate compound wherein the number of isocyanate groups is from 2 to 4. Such a polyisocyanate compound may, for example, be a diisocyanate such as hexamethylene diisocyanate, isophorone diisocyanate, 4,4'-dicyclohexylmethane diisocyanate, tolylene diisocyanate, 4,4'-diphenylmethane diisocyanate or xylylene diisocyanate, or a modified product such as an isocyanurate modified product, burette modified product or polyhydric alcohol modified product of a diisocyanate. As the polyisocyanate compound, preferred is an aliphatic diisocyanate, an alicyclic diisocyanate, or a modified product thereof such as a triisocyanate or tetraisocyanate.

By reacting a reactive compound having a (meth)acryloyl group and one reactive group, a fluorinated monool, and a polyfunctional compound having g number of functional groups in a ratio of (g−1):1:1 by molar ratio of (the reactive compound):(the fluorinated monool):(the polyfunctional compound), compound (1) is produced. For example, by reacting a hydroxyalkyl(meth)acrylate, a fluorinated monool, and a polyisocyanate compound having g number of isocyanate groups, in a molar ratio of (g−1):1:1, it is possible to produce compound (1) having (g−1) number of (meth)acryloyl groups.

The reactive compound, the fluorinated monomer and the polyfunctional compound may be reacted at the same time, or compound (1) may be produced by a method of reacting the fluorinated monool with the polyfunctional compound, followed by a reaction with the reactive compound, or by a method of reacting the reactive compound with the polyfunctional compound, followed by a reaction with the fluorinated monomer.

By the production method (ii), it is possible to produce the above-mentioned compounds (14-1) to (14-6). The compounds (14-1) to (14-6) are obtainable by reacting $G^{10}$-OH as a fluorinated monool, a hydroxyalkyl acrylate, and a triisocyanate in a ratio of 1:2:1 by molar ratio. In the order of the compounds (14-1) to (14-6), the triisocyanate to be used is, an isocyanurate-modified alkylene diisocyanate, an isocyanurate-modified tolylene diisocyanate, an isocyanurate-modified isophorone diisocyanate, a burette-modified alkylene diisocyanate, a glycerol-modified alkylene diisocyanate, or a glycerol-modified alkylene diisocyanate.

Here, the reaction products obtainable by reacting $G^{10}$-OH, a hydroxyalkyl acrylate, and a triisocyanate in a ratio of 1:2:1 by molar ratio, are not necessarily limited only to the compounds (14-1) to (14-6), and as caused by e.g. deviation in the molar ratio of the three components to be reacted, compounds other than the reaction products in a molar ratio of 1:2:1 may sometimes be formed as by-products. Such by-products may, for example, be a compound wherein $G^{10}$ is 2 and the hydroxyalkyl acrylate residue is 1, a compound wherein $G^{10}$ is 3 and the hydroxyalkyl acrylate residue is 0, and a compound wherein $G^{10}$ is 0 and the hydroxyalkyl acrylate residue is 3. The less the by-products, the better, and in some cases, it is possible to reduce the amount of by-products by purifying the reaction product. Further, among by-products, a compound having a hydroxyalkyl acrylate residue may function as the after-mentioned polyfunctional monomer (a1) or monofunctional monomer (a2), and therefore, a compound containing such a by-product may be used without removing such a by-product, unless the amount of such a by-product becomes too much.

In a case other than the case where a triisocyanate compound is used, such formation of by-products is likely to occur in a method for producing compound (1) via a polyfunctional compound. Also in such a case, it is preferred to cope with the matter in the same manner as described above.

Compound (111) can be produced by the following method.

In the presence of a basic compound, $D^1$-$R^F$—O—CF=CF$_2$ is reacted to compound (α1) represented by the following formula (α1) having OH groups at both terminals, to obtain a mixture of compound (α2), compound (α3) and unreacted compound (α1).

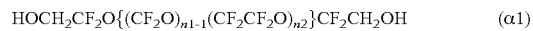

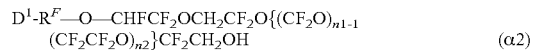

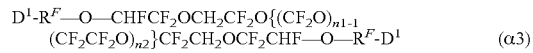

From the above mixture, monofunctional compound (α2) having a OH group remaining at its one terminal, is isolated and used for the following production of a compound.

In the presence of a basic compound such as cesium carbonate, ethylene carbonate is added to compound (α2) while conducting decarboxylation, to obtain compound (α4).

Then, in the presence of a metal complex catalyst such as titanium tetraisobutoxide, ε-caprolactone is anion-polymerized to the compound (α4) to obtain compound (α5).

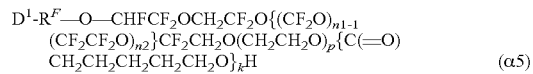

Then, in the presence of a metal catalyst such as tin, acryloyloxyethyl isocyanate is reacted to the compound (α5) to introduce an acryloyl group thereby to obtain compound (111).

In the case of producing compound (112), in the production of compound (111), instead of acryloyloxyethyl isocyanate used, methacryloyloxyethyl isocyanate may be employed.

In the case of producing compound (121), in the production of compound (111), instead of $D^1$-$R^F$—O—CF=CF$_2$ used, $D^1$-$R^F$—CF=CF$_2$ may be employed.

In the case of producing compound (122), in the production of compound (111), instead of $D^1$-$R^F$—O—CF=CF$_2$ used, $D^1$-$R^F$—CF=CF$_2$ may be employed, and instead of acryloyloxyethyl isocyanate used, methacryloyloxyethyl isocyanate may be employed.

In the case of producing compound (131), in the production of compound (111), instead of $D^1$-$R^F$—O—CF=CF$_2$ used, $D^1$-$R^F$—$C_zH_{2z}$—X may be employed (wherein X is a leaving group such as I, Br or Cl).

In the case of producing compound (132), in the production of compound (111), instead of $D^1$-$R^F$—O—CF=CF$_2$ used, $D^1$-$R^F$—$C_zH_{2z}$—X may be employed, and instead of acryloyloxyethyl isocyanate used, methacryloyloxyethyl isocyanate may be employed.

Among compounds (14-1), compound (14-11) wherein $D^1$-$R^{f1}$— is $D^1$-$R^F$—O—CHF—$CF_2$—, each of s, t and u is 6, and each of v and w is 2, can be produced by a method of reacting, in the presence of a metal catalyst such as tin, the above compound (α2), hydroxyethyl acrylate, and a triisocyanate compound being an isocyanurate-modified hexamethylene diisocyanate (a triisocyanate also so-called a cyclic trimer of hexamethylene diisocyanate). To 1 mol of the triisocyanate compound, the total of the active hydrogen in compound (α2) and the active hydrogen in the hydroxyethyl acrylate, may be 3 mol.

To the triisocyanate compound, compound (α2) and the hydroxyethyl acrylate may be added and reacted at the same time, or compound (α2) and the hydroxyethyl acrylate may be sequentially added and reacted, and they are preferably added and reacted in the order of compound (α2) and the hydroxyethyl acrylate.

To 1 mol of the triisocyanate compound, compound (α2) is reacted in an amount of preferably at least 0.001 mol, more preferably at least 0.01 mol, particularly preferably at least 0.1 mol. To 1 mol of the triisocyanate compound, compound (α2) is reacted in an amount of preferably at most 2 mol, more preferably at most 1.5 mol, particularly preferably at most 1 mol.

To 1 mol of the triisocyanate compound, the hydroxyethyl acrylate is reacted in an amount of preferably at least 1 mol, more preferably at least 1.2 mol, particularly preferably at least 1.5 mol. To 1 mol of the triisocyanate compound, the hydroxyethyl acrylate is reacted in an amount of preferably at most 2.5 mol, more preferably at most 2.0 mol, particularly preferably at most 1.8 mol.

Compound (α2), the hydroxyethyl acrylate, and the isocyanurate-modified hexamethylene diisocyanate may be reacted in a solvent.

[Composition for Forming Hard Coat Layer]

The hard coat layer-forming composition of the present invention (hereinafter referred to also as "the present composition") comprises compound (1), a photopolymerizable compound (provided that compound (1) is excluded) and a photopolymerization initiator. The hard coat layer-forming composition of the present invention may further contain a liquid medium or other additives as the case requires.

(Photopolymerizable Compound)

The photopolymerizable compound is a monomer which initiates a polymerization reaction when irradiated with active energy rays in the presence of a photopolymerization initiator which will be described later.

The photopolymerizable compound may be polyfunctional monomer (a1) (hereinafter referred to also as "monomer (a1)") or monofunctional monomer (a2) (hereinafter referred to also as "monomer (a2)"), provided that compound (1) is excluded.

As the photopolymerizable compound, one type may be used alone, or two or more types may be used in combination. With a view to imparting abrasion resistance to a hard coat layer, the photopolymerizable compound is preferably one containing monomer (a1) as an essential component.

Monomer (a1) may be a compound having at least two (meth)acryloyl groups in one molecule. The number of (meth)acryloyl groups per one molecule of the compound is preferably at least 3, particularly preferably from 3 to 30.

With a view to imparting excellent abrasion resistance to a hard coat layer, preferred as monomer (a1) is monomer (a11) which has at least 3 (meth)acryloyl groups in one molecule and which has a molecular weight of at most 120 per one (meth)acryloyl group.

Monomer (a11) may be a compound which is a reaction product of trimethylolpropane, glycerol, pentaerythritol or a multimer thereof (such as polypentaerythritol) with (meth) acrylic acid and which has at least 3, more preferably from 4 to 20, (meth)acryloyl groups. Specific examples include trimethylolpropane tri(meth)acrylate, glycerol tri(meth) acrylate, pentaerythritol tri(meth)acrylate, pentaerythritol tetra(meth)acrylate, dipentaerythritol hexa(meth)acrylate, etc.

As monomer (a1), monomer (a12) which has a urethane bond in its molecule and which has at least three (meth) acryloyl groups in one molecule, is also preferred, since the urethane bond serves as a pseudo cross-linking point by a function of a hydrogen bond, to impart excellent abrasion resistance to a hard coat layer even if the molecular weight per one (meth)acryloyl group is not small.

As monomer (a12), tris(2-acryloyloxyethyl) isocyanurate, the following compounds, etc. may be mentioned.

A compound which is a reaction product of pentaerythritol or polypentaerythritol, a polyisocyanate and a hydroxyalkyl(meth)acrylate and which has at least 3, more preferably from 4 to 20, (meth)acryloyl groups.

A compound which is a reaction product of pentaerythritol poly(meth)acrylate having a hydroxy group or polypentaerythritol poly(meth)acrylate having a hydroxy group, and a polyisocyanate, and which has at least 3, more preferably from 4 to 20, (meth)acryloyl groups.

Monomer (a2) may be a compound having one (meth) acryloyl group in one molecule. Monomer (a2) functions as a reactive diluent and lowers the viscosity of the composition of the present invention to facilitate coating onto a substrate, even in a case where the composition of the present invention contains no liquid medium. Further, even in a case where the composition of the present invention contains a liquid medium, it is effective to adjust the viscosity of the composition or to adjust the physical properties of a hard coat layer.

The following compounds may be mentioned as specific examples.

An alkyl(meth)acrylate wherein the alkyl group has from 1 to 13 carbon atoms, allyl(meth)acrylate, benzyl (meth) acrylate, butoxyethyl(meth)acrylate, butanediol mono (meth)acrylate, butoxytriethylene glycol(meth)acrylate, tert-butylaminoethyl(meth)acrylate, 3-chloro-2-hydroxypropyl (meth)acrylate, 2-cyanoethyl(meth)acrylate, cyclohexyl (meth)acrylate, 2,3-dibromopropyl(meth)acrylate, dicyclopentenyl(meth)acrylate, N,N-diethylaminoethyl (meth)acrylate, N,N-dimethylaminoethyl(meth)acrylate, 2-ethoxyethyl(meth)acrylate, 2-(2-ethoxyethoxy)ethyl (meth)acrylate, 2-ethylhexyl(meth)acrylate, glycerol mono (meth)acrylate, glycidyl(meth)acrylate, heptadecafluorodecyl(meth)acrylate, 2-hydroxyethyl(meth)acrylate, 2-hydroxy-3-(meth)acryloyloxypropyltrimethyl ammonium chloride, 2-hydroxypropyl(meth)acrylate, 3-(meth)acryloxypropyltrimethoxysilane, 2-methoxyethyl(meth)acrylate, methoxydiethylene glycol(meth)acrylate, methoxytriethylene glycol(meth)acrylate, methoxytetraethylene glycol (meth)acrylate, methoxydipropylene glycol(meth)acrylate, methoxylated cyclodecatriene(meth)acrylate, morpholine (meth)acrylate, nonylphenoxypolyethylene glycol(meth) acrylate, nonylphenoxypolypropylene glycol(meth)acrylate, octafluoropentyl(meth)acrylate, phenoxyhydroxypropyl (meth)acrylate, phenoxyethyl(meth)acrylate, phenoxydiethylene glycol(meth)acrylate, phenoxytetraethylene glycol (meth)acrylate, phenoxyhexaethylene glycol(meth)acrylate, phenoxy(meth)acrylate, polypropylene glycol(meth)acrylate, sodium 2-sulfonate ethoxy(meth)acrylate, tetrafluoropropyl(meth)acrylate, tetrahydrofurfuryl(meth)acrylate, trifluoroethyl(meth)acrylate, vinyl acetate, N-vinyl caprolactam, N-vinylpyrrolidone, dicyclopentadienyl(meth)acrylate, isobornyl acrylate, etc.
(Photopolymerization Initiator)

As the photopolymerization initiator, a known photopolymerization initiator may be used. For example, aryl ketone type photopolymerization initiators (e.g. acetophenones, benzophenones, alkylaminobenzophenones, benzyls, benzoins, benzoin ethers, benzyldimethyl ketals, benzoyl benzoates, α-acyloxime esters, etc.), sulfur-containing photopolymerization initiators (e.g. sulfides, thioxanthones, etc.), acyl phosphine oxides (e.g. acyl diaryl phosphine oxides, etc.), and other photopolymerization initiators may be mentioned. As the photopolymerization initiator, one type may be used alone, or two or more types may be used in combination. The photopolymerization initiator may be used in combination with a photosensitizer such as an amine.

As specific examples of the photopolymerization initiator, the following compounds may be mentioned.

4-Phenoxydichloroacetophenone, 4-tert-butyl-dichloroacetophenone, 4-tert-butyl-trichloroacetophenone, diethoxyacetophenone, 2-hydroxy-2-methyl-1-phenylpropan-1-one, 1-(4-isopropylphenyl)-2-hydroxy-2-methylpropan-1-one, 1-(4-dodecylphenyl)-2-methylpropan-1-one, 1-{4-(2-hydroxyethoxy)phenyl}-2-hydroxy-2-methylpropan-1-one, 1-hydroxycyclohexylphenyl ketone, 2-methyl-1-{4-(methylthio)phenyl}-2-morpholinopropan-1-one, benzyl, benzoin, benzoin methyl ether, benzoin ethyl ether, benzoin isopropyl ether, benzoin isobutyl ether, benzyl dimethyl ketal, benzophenone, benzoyl benzoic acid, benzoyl methyl benzoate, 4-phenyl benzophenone, hydroxybenzophenone, acrylated benzophenone, 3,3'-dimethyl-4-methoxybenzophenone, 3,3',4,4'-tetrakis(t-butylperoxycarbonyl)benzophenone, 9,10-phenanthrenequinone, camphor quinone, dibenzosuberone, 2-ethylanthraquinone, 4',4'''-diethylisophtharophenone, (1-phenyl-1,2-propanedione-2(o-ethoxycarbonyl)oxime), α-acyloxime ester, methylphenyl glyoxylate, 4-benzoyl-4'-methyldiphenyl sulfide, thioxanthone, 2-chlorothioxanthone, 2-methylthioxanthone, 2,4-dimethylthioxanthone, isopropylthioxanthone, 2,4-dichlorothioxanthone, 2,4-diethylthioxanthone, 2,4-diisopropylthioxanthone, 2,4,6-trimethylbenzoyldiphenylphosphine oxide, benzoyldiphenylphosphine oxide, 2,6-dimethylbenzoyldiphenylphosphine oxide, bis(2,6-dimethoxybenzoyl)-2,4,4-trimethylpentylphosphine oxide, etc.
(Liquid Medium)

The present composition may further contain a liquid medium as the case requires.

By containing a liquid medium, the present composition can be adjusted in its formulation, viscosity, surface tension, etc. and can be controlled to have liquid physical properties suitable for the coating method.

As the liquid medium, an organic solvent is preferred. As the organic solvent, an organic solvent having a boiling point suitable for the coating method for the present composition is preferred.

The organic solvent may be a fluorinated organic solvent or a non-fluorinated organic solvent, or may contain both solvents.

As the fluorinated organic solvent, the above-mentioned fluoroalkane, fluoroaromatic compound, fluoroalkyl ether, fluoroalkylamine, fluoroalcohol, etc. may be mentioned.

Since compound (1) is readily soluble, the fluorinated organic solvent is preferably a fluoroalkane, a fluoroaromatic compound, a fluoroalcohol or a fluoroalkyl ether, particularly preferably a fluoroalcohol or a fluoroalkyl ether.

As the non-fluorinated organic solvent, a compound composed solely of hydrogen atoms and carbon atoms, or a compound composed solely of hydrogen atoms, carbon atoms and oxygen atoms, is preferred, and the above-mentioned hydrocarbon type organic solvent, alcohol type organic solvent, ketone type organic solvent, ether type organic solvent, glycol ether type organic solvent or ester type organic solvent may be mentioned.

Since compound (1) is readily soluble, the non-fluorinated organic solvent is particularly preferably a glycol ether type organic solvent or a ketone type organic solvent.

The liquid medium is preferably at least one organic solvent selected from the group consisting of a fluoroalkane, a fluoroaromatic compound, a fluoroalkyl ether, a fluoroalcohol, a compound composed solely of hydrogen atoms and carbon atoms, and a compound composed solely of hydrogen atoms, carbon atoms and oxygen atoms. Particularly preferred is a fluorinated organic solvent selected from a fluoroalkane, a fluoroaromatic compound, a fluoroalkyl ether and a fluoroalcohol.

With a view to increasing the solubility of compound (1), the liquid medium preferably contains at least 90 mass % in total, based on the entire liquid medium, of at least one organic solvent selected from the group consisting of, as a fluorinated organic solvent, a fluoroalkane, a fluoroaromatic compound, a fluoroalkyl ether, a fluoroalcohol, and, as a non-fluorinated organic solvent, a compound composed solely of hydrogen atoms, carbon atoms and oxygen atoms.
(Other Additives)

The present composition may further contain other additives as the case requires.

Other additives may, for example, be colloidal silica, a photosensitizer, an ultraviolet absorber, a photostabilizer, a thermal curing stabilizer, an antioxidant, a leveling agent, a defoaming agent, a thickener, an antisettling agent, a pigment, a dye, a dispersant, an antistatic agent, a surfactant (such as an antifogging agent, a leveling agent, etc.), metal oxide particles, various resins (such as an epoxy resin, an unsaturated polyester resin, a polyurethane resin, etc.), etc.

Further, at the time of using compound (1), compounds (hereinafter referred to also as impurities) which are unavoidable by the production of compound (1) may be accompanied. Specifically, they are by-products formed in the step of producing compound (1) or components included in the step of producing compound (1). The content of such impurities is preferably at most 5 mass %, particularly preferably at most 2 mass %, to compound (1) (100 mass %). When the content of impurities is within such a range, it is possible to impart excellent antifouling properties (oily ink repellency, fingerprint stain removability) and lubricity to a hard coat layer.

The identification and quantitative analyses of by-products in compound (1) are carried out by $^1$H-NMR (300.4 MHz) and $^{19}$F-NMR (282.7 MHz).
(Composition)

The content of compound (1) is preferably from 0.01 to 5 mass %, more preferably from 0.02 to 4 mass %, particularly preferably from 0.05 to 3 mass %, in the solid content (100 mass %) of the present composition. When the content of compound (1) is within such a range, the storage stability of the present composition, and the appearance, abrasion resistance, antifouling properties (oily ink repellency, fingerprint stain removability) and lubricity of the hard coat layer will be excellent.

Here, the solid content in the present composition is meant for all components excluding the liquid medium. Therefore, even if the present composition contains a liquid component (e.g. monomer (a1) or monomer (a2)) other than the liquid medium, the solid content of the present composition excluding the liquid medium is 100 mass %.

The content of the photopolymerizable compound is preferably from 20 to 98.99 mass %, more preferably from 50 to 98.99 mass %, further preferably from 60 to 98.99 mass %, particularly preferably from 80 to 98.99 mass %, in the solid content (100 mass %) of the present composition. When the content of the photopolymerizable compound is within such a range, the storage stability of the present composition, and the appearance, abrasion resistance, antifouling properties (oily ink repellency, fingerprint stain removability) and lubricity of the hard coat layer will be excellent.

The content of the photopolymerization initiator is preferably from 1 to 15 mass %, more preferably from 3 to 15 mass %, particularly preferably from 3 to 10 mass %, in the solid content (100 mass %) of the present composition. When the content of the photopolymerization initiator is within such a range, the compatibility with the photopolymerizable compound will be excellent. Further, the curing properties of the present composition will be excellent, and a cured film to be formed will be excellent in hardness.

When the liquid medium is contained, the content of the liquid medium is preferably from 5 to 80 mass %, more preferably from 10 to 70 mass %, particularly preferably from 20 to 60 mass %, in the present composition (100 mass %).

When other additives are contained, the content of other additives is preferably from 0.5 to 20 mass %, more preferably from 1 to 15 mass %, particularly preferably from 1 to 10 mass %, in the solid content (100 mass %) of the present composition.

The solid content concentration in the present composition may be adjusted so that the liquid physical properties would be suitable for the coating method. In a case where a liquid medium is contained, the solid content concentration in the present composition may be adjusted, for example, to be preferably from 30 to 90 mass %, particularly preferably from 40 to 80 mass %.

[Article]

The article of the present invention comprises a substrate and a hard coat layer formed from the present composition. With a view to improving the adhesion between the substrate and the hard coat layer, it may further have a primer layer between the substrate and the hard coat layer. That is, as the article of the present invention, an article having a hard coat layer formed from the present composition laminated directly on the surface of at least one side of the substrate, or an article having a hard coat layer formed from the present composition laminated, via a primer layer, on the surface of at least one side of the substrate, is preferred.

From the viewpoint of the abrasion resistance and antifouling properties, the thickness of the hard coat layer is preferably from 0.5 to 20 µm, particularly preferably from 1 to 15 µm.

(Substrate)

The substrate is a main body portion of various articles (such as an optical lens, a display, an optical recording medium, etc.) required to have abrasion resistance and antifouling properties, or a member constituting the surface of such an article.

The material for the substrate surface may, for example, be a metal, a resin, glass, ceramics, stone or a composite material thereof. The material for the substrate surface in an optical lens, a display or an optical recording medium, is preferably glass or transparent resin substrate.

The glass is preferably soda lime glass, alkali aluminosilicate glass, borosilicate glass, alkali-free glass, crystal glass or quartz glass, particularly preferably chemically tempered soda lime glass, chemically tempered alkali aluminosilicate glass or chemically tempered borosilicate glass. The material for the transparent resin substrate is preferably an acrylic resin or a polycarbonate resin.

The present composition is photocurable and requires no heating for its curing, and therefore, it is suitably used at the time of forming a hard coat layer on a substrate made of a resin with a relatively low heat resistance as compared with e.g. glass.

By using the present composition, it is possible to obtain a hard coat layer excellent in abrasion resistance, antifouling properties (oily ink repellency, fingerprint stain removability) and lubricity. An article having such a hard coat layer is suitable as a member to constitute a touch panel. The touch panel is an input device of an input/display apparatus (touch panel apparatus) having a display device combined with the input device for inputting a contact position information upon touching with e.g. a finger. The touch panel is constituted by a substrate and, depending upon the input detection system, a transparent conductive film, electrodes, a wiring, IC, etc. By using the side having a hard coat layer, of the article, as the input side of a touch panel, it is possible to obtain a touch panel having excellent antifouling properties (oily ink repellency, fingerprint stain removability) and lubricity. When the lubricity is excellent, the touch feeling of the touch panel will be excellent, and the operation efficiency will be improved.

The material for the substrate of the touch panel has translucency. Specifically, the normal incidence visible light transmittance in accordance with JIS R1306 is at least 25%.

(Primer Layer)

As the primer layer, a known one may be mentioned. The primer layer may, for example, be formed by applying a primer layer-forming composition containing a liquid medium on the surface of a substrate and then removing the liquid medium by vaporization.

(Process for Producing Article)

The article may, for example, be produced via the following steps (I) and (II). The step (I) is conducted as the case requires.

Step (I): A step of applying a primer layer-forming composition on the surface of a substrate to form a primer layer.

Step (II): A step of applying the present composition on the surface of a substrate or a primer layer to obtain a coating film, removing a liquid medium in a case where the present composition contains the liquid medium, and photocuring the coating film to form a hard coat layer.

Here, the process of removing the liquid medium by vaporization from the coating film of the present composition containing the liquid medium will be referred to also as drying.

Step (I):

As the coating method, a known method may suitably be used. Such a coating method may, for example, be a bar coating method, a spin coating method, a wipe coating method, a spray coating method, a squeegee coating method, a dip coating method, a die coating method, an ink jet coating method, a flow coating method, a roll coating method, a casting method, a Langmuir-Blodgett method or a gravure coating method.

The drying temperature is preferably from 50 to 140° C.

The drying time is preferably from 0.5 minute to 3 hours.

Step (II):

As the coating method, such a known coating method as exemplified in step (I) may be mentioned.

In a case where the present composition contains a liquid medium, the liquid medium is removed from the coating film to form a dried film, before photocuring. As the method for removing the liquid medium, a known method may suitably be used.

The drying method may, for example, be heating, vacuuming or a method of heating under reduced pressure. Further, the obtained dried film preferably contains a liquid medium in an amount of less than 10 mass %, particularly preferably less than 1 mass %.

The temperature in the case of heating is preferably from 50 to 120° C.

The time for removing the solvent is preferably from 0.5 minute to 3 hours.

The photocuring is applied to a coating film in a case where the present composition contains no liquid medium, or it is applied to a dried film in a case where the present composition contains a liquid medium.

The photocuring is conducted by irradiation with active energy rays.

The active energy rays may, for example, be ultraviolet rays, electron rays, X-rays, radioactive rays, radio frequency radiation, etc., and ultraviolet rays with a wavelength of from 180 to 500 nm are economically preferred.

As active energy ray sources, an ultraviolet irradiation apparatus (a xenon lamp, a low-pressure mercury lamp, a high-pressure mercury lamp, an ultrahigh-pressure mercury lamp, a metal halide lamp, a carbon arc lamp, a tungsten lamp, etc.), an electron beam irradiation apparatus, an X-ray irradiation apparatus, a high-frequency apparatus, etc. may be used.

The time for irradiation with active energy rays may suitably adjusted depending upon such conditions as the type of the compound (1), the type of the photopolymerizable compound, the type of the photopolymerization initiator, the thickness of the coating film, the active energy ray source, etc. Usually, by irradiation for from 0.1 to 60 seconds, the purpose may be accomplished.

For the purpose of completing the curing reaction, heating may be conducted after irradiation with active energy rays. The heating temperature is preferably from 50 to 120° C.

EXAMPLES

Now, the present invention will be described in further detail with reference with Examples, but it should be understood that the present invention is by no means restricted by these Examples. In the following, "%" is "mass %" unless otherwise specified. Further, Ex. 1 to 4 and 9 to 18 are Examples of the present invention, and Ex. 5 to 8 and 19 to 20 are Comparative Examples.

Abbreviations used in Examples have the following meanings.

TMS: tetramethylsilane,

AC-2000: $C_6H_{13}H$, tradename, manufactured by Asahi Glass Company, Limited,

AE-3000: $CF_3CH_2OCF_2CF_2H$, tradename, manufactured by Asahi Glass Company, Limited, AK-225: dichloropentafluoropropane, DBTDL: dibutyltin dilaurate, R-113: $CCl_2FCClF_2$.

L: liter,

Mn: number average molecular weight.

[Measurements, Evaluations]

(Number Average Molecular Weight (Mn))

Gel permeation chromatography (GPC) of several monodisperse polymethyl methacrylates different in polymerization degree, commercially available as standard samples for measuring molecular weights, was measured by means of a commercially available GPC measuring apparatus (manufactured by Tosoh Corporation, apparatus name: HLC-8220GPC) using, as an eluent, a mixed solvent of AK-225:hexafluoroisopropanol=99:1 (volume ratio), and a calibration curve was prepared based on the relation between the molecular weight of the polymethyl methacrylate and the retention time.

A fluorinated compound was diluted with the above mixed solvent to 1.0 mass % and then passed through a filter of 0.5 μm, whereupon with respect to the fluorinated compound, GPC was measured by means of the above GPC measuring apparatus.

Using the above calibration curve, the GPC spectrum of the fluorinated compound was subjected to a computer analysis to obtain the number average molecular weight (Mn) of the fluorinated compound.

(Proportion of Fluorine Atoms)

The proportion (mass %) of fluorine atoms in a fluorinated compound was calculated based on the integration ratio in $^1$H-NMR (300.4 MHz) and $^{19}$F-NMR (282.7 MHz) using hexafluorometaxylene as the internal standard.

(Water Contact Angle)

In accordance with JIS R3257 "Method for testing wettability of substrate glass surface", water droplets were placed at three locations on a hard coat layer, and with respect to each droplet, the water contact angle was measured by a sessile drop method. The droplets were about 2 μL/droplet, and the measurement was conducted at 20° C. The contact angle is shown by an average value (n=3) of the three measured values. Here, from the viewpoint of antifouling properties, the water contact angle is preferably at least 100°.

(Oleic Acid Contact Angle)

In accordance with JIS R3257 "Method for testing wettability of substrate glass surface", oleic acid droplets were placed at three locations on a hard coat layer, and with respect to each oleic acid droplet, the oleic acid contact angle was measured by a sessile drop method. The droplets were about 2 μL/droplet, and the measurement was conducted at 20° C. The contact angle is shown by an average value (n=3) of the three measured values. Here, from the viewpoint of antifouling properties, the oleic acid contact angle is preferably at least 65°.

(Compatibility)

The appearance of a hard coat layer-forming composition immediately after preparation was visually evaluated in accordance with the following standards.

○ (Good): The solution is uniform without turbidity.

x (No good): Turbidity is observed.

(Storage Stability)

A hard coat layer-forming composition was left to stand at room temperature for 3 months, whereupon the appearance of the hard coat layer-forming composition was visually evaluated.

○ (Good): The solution is uniform without turbidity.
x (No good): Turbidity is observed.
(Appearance of Hard Coat Layer)
In accordance with the following standards, the appearance of a hard coat layer was visually evaluated.
○ (Good): No foreign matter is observed, and the film thickness is uniform.
x (Permissive): No foreign matter is observed, but unevenness is observed in the film thickness.
x (No good): Foreign matters are observed, and unevenness is observed in the film thickness.
(Oily Ink Repellency)
On the surface of a hard coat layer, a line was drawn by a felt pen (manufactured by Zebra Co., Ltd., tradename: Mackee Extra-thick Black), and the adhesion state of an oily ink was visually observed and evaluated. The evaluation standards are as follows.
⊚ (Excellent): The oily ink is repelled in the form of balls.
○ (Good): The oily ink is not repelled in the form of balls, but is repelled in the form of a line, and the line breadth is less than 50% of the breadth of the pen tip of the felt pen.
Δ (Permissive): The oily ink is not repelled in the form of balls, but is repelled in the form of a line, and the line breadth is at least 50% and less than 100% of the breadth of the pen tip of the felt pen.
x (No good): The oily ink is not repelled in the form of balls or in the form of a line, and the line is drawn well on the surface.
(Fingerprint Stain Removability)
An artificial fingerprint liquid (a liquid composed of oleic acid and squalene) was attached on a flat surface of a silicon rubber stopper, and an excess oil was wiped off with a non-woven fabric (manufactured by Asahi Kasei Corporation, tradename: Bemcot M-3) to prepare a fingerprint stamp. The fingerprint stamp was put on an article having a hard coat layer and pressed under a load of 1 kg for 10 seconds. Then, with respect to the portion where the fingerprint was impressed, wiping was conducted under a load of 500 g by means of a reciprocating traverse testing apparatus (manufactured by KNT) having tissue paper attached. The haze was visually observed after every one reciprocation for wiping, and the fingerprint stain removability was evaluated by visually observing the haze up to after 10 reciprocations. The evaluation standards are as follows.
○ (Good): No haze is visually observed.
Δ (Permissive): A haze is slightly visually observed.
x (No good): A haze is distinctly visually observed.
(Abrasion Resistance)
With respect to an article having a hard coat layer, by means of a reciprocating traverse testing apparatus (manufactured by KNT), steel wool (manufactured by Nippon Steel Wool Co., Ltd., Bonstar #0000) was reciprocated 100 times under a load of 1,000 g, whereupon the water contact angle and the oleic acid contact angle were measured.
The smaller the decrease in the water contact angle and the oleic acid contact angle after the abrasion by the steel wool, the smaller the decrease in performance due to the abrasion, and the better the abrasion resistance.
(Pencil Hardness)
Measured in accordance with JIS K5600.
(Dynamic Friction Coefficient)
By means of a variable normal load friction and wear measurement system HHS2000 (manufactured by SHINTO Scientific Co., Ltd.), the dynamic friction coefficient of a substrate having a hard coat layer against an artificial skin (PBZ13001, manufactured by Idemitsu Technofine) was measured under conditions of a contact area of 3 cm×3 cm and a load of 100 g.
The smaller the dynamic friction coefficient, the better the lubricity.
[Compounds]
(Photopolymerizable Compounds)
(a-1): Dipentaerythritol hexaacrylate (corresponding to monomer (a11)).
(a-2): Tris(acryloyloxyethyl) isocyanurate (corresponding to monomer (a12)).
(Photopolymerization initiator)
(b-1): 2-Methyl-1-{4-(methylthio)phenyl}-2-morpholino-propan-1-one.
(Organic Solvents)
(c-1): 2,2,3,3-Tetrafluoropropanol.
(c-2): 1,1,2,2,3,3,4-Heptafluorocyclopentane.
(c-3): Propylene glycol monomethyl ether acetate.
(c-4): Propylene glycol monomethyl ether.

[Ex. 1] Example for Producing Compound (111-1)

Ex. 1-1

Into a 500 mL three-necked round-bottomed flask, 1.04 g of potassium hydroxide was introduced, and 83 g of tert-butanol and 125 g of 1,3-dis(trifluoromethyl)benzene were added. The potassium hydroxide was dissolved by stirring at room temperature, and 250 g of compound ($\alpha$1) (FLUOROLINK D10/H: tradename, manufactured by Solvay Solexis K.K.) was added thereto, followed by stirring for one hour. At room temperature, 38.2 g of perfluoro(propyl vinyl ether) ($CF_3CF_2CF_2$—O—$CF=CF_2$) was added, followed by stirring for further 24 hours. A hydrochloric acid aqueous solution was added for neutralization, and water was further added for liquid separation treatment. After washing three times with water, the organic phase was recovered and concentrated by an evaporator to obtain 288.0 g of a reaction crude liquid. It was again diluted with 144 g of AC-2000 and developed and fractionated by silica gel column chromatography (developing solvent: AC-2000 and AE-3000), whereby 136.2 g (yield: 47%) of compound ($\alpha$2-1) was obtained.

$$CF_3CF_2CF_2\text{—O—}CHFCF_2\text{—O—}CH_2\text{—}CF_2O\{(CF_2O)_{n1\text{-}1}(CF_2CF_2O)_{n2}\}CF_2CH_2OH \quad (\alpha\text{2-1})$$

Average value of (n1–1): 8.
Average value of (n2): 10.
NMR Spectra of Compound ($\alpha$2-1):
$^1$H-NMR (300.4 MHz, solvent: deuterated chloroform, standard: TMS) δ (ppm): 3.9, 4.2, 5.9.
$^{19}$F-NMR (282.7 MHz, solvent: deuterated chloroform, standard: $CFCl_3$) δ (ppm): −52.3 to −55.7, −78.7, −80.7, −81.3, −82.1, −83.4, −85.3 to −88.2, −89.4 to −91.1, −130.5, −145.2.

Ex. 1-2

Into a 50 mL four-necked flask equipped with a stirrer and a condenser, 391 mg of cesium carbonate, 1.50 g of compound ($\alpha$2-1) and 106 mg of ethylene carbonate were added, and heated and stirred at 160° C. for 36 hours. To the obtained solution, 15 g of AK-225 and 10 g of dilute hydrochloric acid were added. The organic layer and the aqueous layer were separated, and the organic layer was washed three times with 30 mL of ion-exchanged water and dehydrated with sodium sulfate, followed by distilling off the solvent under reduce pressure to obtain 1.07 g of compound (α4-1).

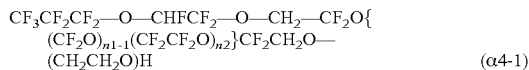
(α4-1)

NMR Spectra of Compound (α4-1):
$^1$H-NMR (300.4 MHz, solvent: deuterated acetone+R-113, standard: TMS) δ (ppm): 3.69, 4.04, 4.64, 6.40 to 6.83.
$^{19}$F-NMR (282.7 MHz, solvent: deuterated acetone+R-113, standard: CFCl$_3$) δ (ppm): −51.7 to −58.4, −78.6, −80.6, −82.3, −85.2 to −87.6, −89.0 to −92.1, −130.7, −146.3.

Ex. 1-3

Into a 50 mL two-necked flask equipped with a stirrer and a condenser, 1.3 mg of titanium tetraisobutoxide, 500 mg of compound (α4-1) and 81 mg of ε-caprolactone were added and heated at 160° C. for 7 hours to obtain 580 mg of compound (α5-1).

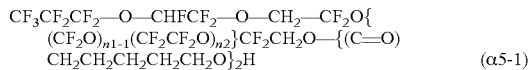
(α5-1)

NMR Spectra of Compound (α5-1):
$^1$H-NMR (300.4 MHz, solvent: deuterated acetone+R-113, standard: TMS) δ (ppm): 1.64, 1.79, 2.30, 2.60, 3.61 to 4.73, 6.55 to 6.85.
$^{19}$F-NMR (282.7 MHz, solvent: deuterated acetone+R-113, standard: CFCl$_3$) δ (ppm): −51.8 to −56.3, −78.8, −80.8, −82.3, −85.2 to −87.5, −88.7 to −91.9, −130.6, −146.3.

Ex. 1-4

Into a 50 mL two-necked flask equipped with a stirrer, 750 mg of AK-225, 250 mg of acetone, 0.8 mg of 2,6-di-tert-butyl-para-cresol as a polymerization inhibitor, 15.7 mg of 2-acryloyloxyethyl isocyanate, 0.06 mg of DBTDL and 200 mg of compound (α5-1) were added and stirred at 40° C. for 24 hours. Thereafter, the solvent was distilled off under reduced pressure to obtain a mixture of compound (111-1) and the above polymerization inhibitor. The content of compound (111-1) in the mixture was 99.6 mass %. The number average molecular weight (Mn) of compound (111-1) was 2,200, and the proportion of fluorine atoms was 61 mass %.

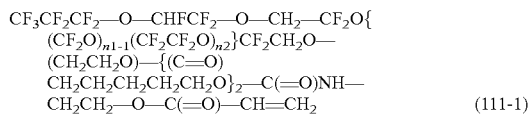
(111-1)

NMR Spectra of Compound (111-1):
$^1$H-NMR (300.4 MHz, solvent: deuterated acetone+R-113, standard: TMS) δ (ppm): 0.80 to 2.11, 3.30 to 4.77, 5.57 to 6.52, 6.52 to 6.87.
$^{19}$F-NMR (282.7 MHz, solvent: deuterated acetone+R-113, standard: CFCl$_3$) δ (ppm): −52.4, −54.1, −55.9, −78.3 to −78.9, −80.8, −85.2 to −87.4, −88.9 to −91.9, −130.7, −146.5.

[Ex. 2] Example for Forming Hard Coat Layer

Into a 30 mL vial container, 2 mg of the above mixture containing 99.6 mass % of compound (111-1) obtained in Ex. 1, 94 mg of photopolymerizable compound (a-1), 94 mg of photopolymerizable compound (a-2), 11.8 mg of photopolymerization initiator (b-1), 18 mg of organic solvent (c-2) and 117 mg of organic solvent (c-4) were put and stirred for one hour at room temperature in a light-shielded state to obtain a hard coat layer-forming composition (1).

Then, on the surface of a polyethylene terephthalate (hereinafter referred to also as "PET") substrate, the hard coat layer-forming composition (1) is applied by bar coating to form a coating film, which was dried for one minute on a hot plate of 50° C. to form a dried film on the surface of the substrate. Then, by means of a high pressure mercury lamp, ultraviolet rays (light quantity: 300 mJ/cm$^2$, integrated energy amount of ultraviolet rays with a wavelength of 365 nm) were applied to form a hard coat layer having a thickness of 5 μm on the surface of the substrate.

The composition of the hard coat layer-forming composition (1), and the evaluation results of the hard coat layer, are shown in Table 1.

[Ex. 3] Example for Producing Compound (14-11a)

Into a 50 mL two-necked flask equipped with a stirrer, 1.0 g of isocyanurate-modified hexamethylene diisocyanate (cyclic trimer of hexamethylene diisocyanate, manufactured by Asahi Kasei Chemicals Corporation, tradename: DURANATE THA-100) and 6.0 g of AK-225 were put, and 7.5 mg of DBTDL and 0.3 mg of 2,6-di-tert-butyl-para-cresol were added. While stirring at room temperature in a nitrogen atmosphere, a solution having 0.98 g of compound (a 2-1) obtained in Ex. 1-1 dissolved in 1.0 g of AK-225, was dropwise added over one hour, followed by stirring at room temperature for 12 hours. The temperature was raised to 40° C., and 0.76 g of 2-hydroxyethyl acrylate was dropwise added in 2 minutes, followed by stirring for 12 hours. Upon confirming by the infrared absorption spectrum that absorption of an isocyanate group disappeared completely, the obtained reaction solution was concentrated by an evaporator, to obtain 2.87 g of a mixture comprising compound (14-11a) wherein one of G$^1$ to G$^3$ in the following formula (13) is a group represented by the following formula (14a), and the rest are groups represented by the following formula (15); a compound wherein two of G$^1$ to G$^3$ are groups represented by the following formula (14a), and the rest is a group represented by the formula (15); a compound wherein all of G$^1$ to G$^3$ are groups represented by the following formula (14a); and a compound wherein all of G$^1$ to G$^3$ are groups represented by the following formula (15). As the mixture, the number average molecular weight (Mn) was 1,400, and the proportion of fluorine atoms was 23 mass %.

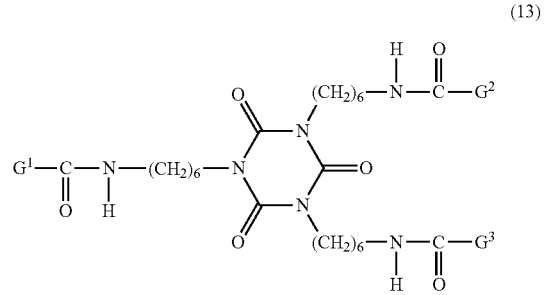
(13)

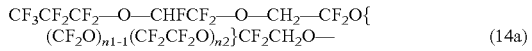
(14a)

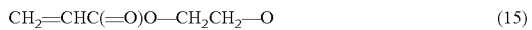
(15)

NMR Spectra of Compound (14-11a):

$^1$H-NMR (300.4 MHz, solvent: deuterated chloroform+R-113, standard: TMS) δ (ppm): 1.19 to 1.76, 3.19, 3.29, 3.74, 3.88, 4.30, 4.85 to 5.28, 5.84, 6.15, 6.45.

$^{19}$F-NMR (282.7 MHz, solvent: deuterated chloroform+R-113, standard: CFCl$_3$) δ (ppm): −52.3, −53.9, −55.6, −78.5, −80.6, −82.2, −86.8, −89.4, −91.0, −130.6, −145.0.

[Ex. 4] Example for Forming Hard Coat Layer

Into a 30 mL vial container, 1 mg of the mixture containing compound (14-11a) obtained in Ex. 3, 94 mg of photopolymerizable compound (a-1), 94 mg of photopolymerizable compound (a-2), 11 mg of photopolymerization initiator (b-1), 18 mg of organic solvent (c-1) and 117 mg of organic solvent (c-4) were put and stirred for one hour at room temperature in a light-shielded state to obtain a hard coat layer-forming composition (2).

Then, on the surface of a substrate, a hard coat layer having a thickness of 5 μm was formed in the same manner as in Ex. 2 except that the hard coat layer-forming composition (2) was used instead of the hard coat layer-forming composition (1).

The composition of the hard coat layer-forming composition (2), and the evaluation results of the hard coat layer, are shown in Table 1.

[Ex. 5] Example for Producing Polymer (A)

In accordance with the method disclosed in Example 1 in Patent Document 1, a fluorinated polymer (polymer (A)) obtainable by copolymerizing a fluorinated compound having acryloyloxy groups at both terminals of a poly(oxyperfluoroalkylene) chain composed of a combination of (CF$_2$O) and (CF$_2$CF$_2$O), with hydroxyethyl methacrylate, followed by a reaction with 2-acryloyloxyethyl isocyanate, was synthesized (number average molecular weight (Mn): 2,400). The proportion of fluorine atoms in polymer (A) was 11 mass %.

[Ex. 6] Example for Forming Hard Coat Layer

Into a 30 mL vial container, 2 mg of the polymer (A) obtained in Ex. 5, 94 mg of photopolymerizable compound (a-1), 94 mg of photopolymerizable compound (a-2), 11.8 mg of photopolymerization initiator (b-1) and 134.5 mg of organic solvent (c-4) were put and stirred for one hour at room temperature in a light-shielded state to obtain a hard coat layer-forming composition (3).

Then, on the surface of a substrate, a hard coat layer having a thickness of 5 μm was formed in the same manner as in Ex. 2 except that the hard coat layer-forming composition (3) was used instead of the hard coat layer-forming composition (1).

The composition of the hard coat layer-forming composition (3), and the evaluation results of the hard coat layer, are shown in Table 1.

[Ex. 7] Example for Producing Compound (B)

As compound (B), water/oil repellency-imparting agent (B-13) disclosed in an Example in Patent Document 2, which has a perfluoromethyl group at its molecular terminal and which has such a structure that an oxyperfluoroalkylene group is bonded to the perfluoromethyl group, was synthesized in accordance with the method disclosed in the Example in Patent Document 2, and used as compound (B).

The number average molecular weight (Mn) of compound (B) was 1,800, and the proportion of fluorine atoms was 42 mass %.

[Ex. 8] Example for Forming Hard Coat Layer

Into a 30 mL vial container, 0.2 mg of compound (B) obtained in Ex. 7, 94 mg of photopolymerizable compound (a-1), 94 mg of photopolymerizable compound (a-2), 11.8 mg of photopolymerization initiator (b-1), 18 mg of organic solvent (c-3) and 117 mg of organic solvent (c-4) were put and stirred for one hour at room temperature in a light-shielded state to obtain a hard coat layer-forming composition (4).

Then, on the surface of a substrate, a hard coat layer having a thickness of 5 μm was formed in the same manner as in Ex. 2 except that the hard coat layer-forming composition (4) was used instead of the hard coat layer-forming composition (1).

The composition of the hard coat layer-forming composition (4), and the evaluation results of the hard coat layer, are shown in Table 1.

[Ex. 9] Example for Producing Compound (14-11b)

Ex. 9-1

Compound (α6-1) (yield: 44.8%) was obtained in the same manner as in (Ex. 1-1) except that instead of compound (α1), compound (α6) (FLUOROLINK D4000: tradename, manufactured by Solvay Solexis K.K.) was used.

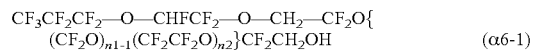

$CF_3CF_2CF_2$—O—$CHFCF_2$—O—$CH_2$—$CF_2$O{$(CF_2O)_{n1-1}(CF_2CF_2O)_{n2}$}$CF_2CH_2OH$     (α6-1)

Average value of the number of units n1−1: 21.
Average value of the number of units n2: 20.

NMR Spectra of Compound (α6-1):

$^1$H-NMR (300.4 MHz, solvent: deuterated chloroform, standard: TMS) δ (ppm): 3.9, 4.2, 5.8 to 6.0.

$^{19}$F-NMR (282.7 MHz, solvent: deuterated chloroform, standard: CFCl$_3$) δ (ppm): −52.4 to −55.8, −78.8, −80.8, −81.4, −82.2, −83.5, −85.3 to −88.2, −89.4 to −91.1, −130.5, −145.1.

Ex. 9-2

In the same manner as in (Ex. 3) except that instead of compound (α2-1), 2.42 g of compound (α6-1) was used, a mixture comprising compound (14-11b) wherein one of G$^1$ to G$^3$ in the formula (13) is a group represented by the following formula (14b), and the rest are groups represented by the following formula (15); a compound wherein two of G$^1$ to G$^3$ are groups represented by the following formula (14b), and the rest is a group represented by the following formula (15); a compound wherein all of G$^1$ to G$^3$ are groups represented by the following formula (14b); and a compound wherein all of G$^1$ to G$^3$ are groups represented by the following formula (15), was obtained. As the mixture, the number average molecular weight (Mn) was 4,800, and the proportion of fluorine atoms was 37 mass %.

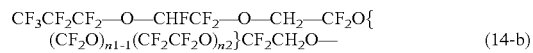

$CF_3CF_2CF_2$—O—$CHFCF_2$—O—$CH_2$—$CF_2$O{$(CF_2O)_{n1-1}(CF_2CF_2O)_{n2}$}$CF_2CH_2O$—     (14-b)

Average value of the number of units n1−1: 21.
Average value of the number of units n2: 20.

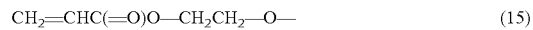

$CH_2$=$CHC$(=O)O—$CH_2CH_2$—O—     (15)

NMR Spectra of Compound (14-11b):
$^1$H-NMR (300.4 MHz, solvent: deuterated chloroform+ R-113, standard: TMS) δ (ppm): 1.19 to 1.76, 3.19, 3.29, 3.74, 3.88, 4.30, 4.85 to 5.28, 5.84, 6.15, 6.45.
$^{19}$F-NMR (282.7 MHz, solvent: deuterated chloroform+ R-113, standard: CFCl$_3$) δ (ppm): −52.3, −53.9, −55.6, −78.5, −80.6, −82.2, −86.8, −89.4, −91.0, −130.6, −145.0.

[Ex. 10] Example for Forming Hard Coat Layer

A hard coat layer-forming composition (5) and a hard coat layer were obtained in the same manner as in Ex. 3 except that instead of compound (14-11a), compound (14-11 b) obtained in Ex. 9 was used.

The composition of the hard coat layer-forming composition (5), and the evaluation results of the hard coat layer, are shown in Table 1.

[Ex. 11] Example for Producing Compound (14-12b)

In the same manner as in Ex. 9-2 except that instead of hydroxyethyl acrylate, 0.94 g of hydroxybutyl acrylate was used, a mixture comprising compound (14-12b) wherein one of G$^1$ to G$^3$ in the formula (13) is a group represented by the following formula (14b), and the rest are groups represented by the following formula (16); a compound wherein two of G$^1$ to G$^3$ are groups represented by the following formula (14b), and the rest is a group represented by the formula (16); a compound wherein all of G$^1$ to G$^3$ are groups represented by the following formula (14b); and a compound wherein all of G$^1$ to G$^3$ are groups represented by the following formula (16), was obtained. As the mixture, the number average molecular weight (Mn) was 4,900, and the proportion of fluorine atoms was 36 mass %.

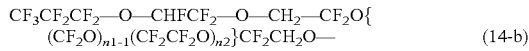
(14-b)

Average value of the number of units n1−1: 21.
Average value of the number of units n2: 20.

(16)

NMR Spectra of Compound (14-12b):
$^1$H-NMR (300.4 MHz, solvent: deuterated chloroform+ R-113, standard: TMS) δ (ppm): 1.19 to 1.76, 3.19, 3.29, 3.74, 3.88, 4.30, 4.85 to 5.28, 5.84, 6.15, 6.45.
$^{19}$F-NMR (282.7 MHz, solvent: deuterated chloroform+ R-113, standard: CFCl$_3$) δ (ppm): −52.3, −53.9, −55.6, −78.5, −80.6, −82.2, −86.8, −89.4, −91.0, −130.6, −145.0.

[Ex. 12] Example for Forming Hard Coat Layer

A hard coat layer-forming composition (6) and a hard coat layer were obtained in the same manner as in Ex. 3 except that instead of compound (14-11a), compound (14-12b) obtained in Ex. 11 was used.

The composition of the hard coat layer-forming composition (6), and the evaluation results of the hard coat layer, are shown in Table 2.

[Ex. 13] Example for Producing Compound (14-11c)

Ex. 13-1

Compound (α7-1) (yield: 39.1%) was obtained in the same manner as in (Ex. 1-1) except that instead of perfluoro (propyl vinyl ether) (CF$_3$CF$_2$CF$_2$—O—CF=CF$_2$), 59.7 g of CF$_3$CF$_2$CF$_2$—O—CF(CF$_3$)CF$_2$—O—CF=CF$_2$ was used.

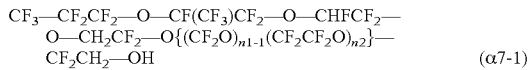
(α7-1)

Average value of the number of units n1−1: 8.
Average value of the number of units n2: 10.
NMR Spectra of Compound (α7-1):
$^1$H-NMR (300.4 MHz, solvent: CDCl$_3$, standard: TMS) δ (ppm): 3.9, 4.2, 5.8 to 6.0.
$^{19}$F-NMR (282.7 MHz, solvent: CDCl$_3$, standard: CFCl$_3$) δ (ppm): −52.4 to −55.8, −78.9, −80.9, −81.4, −82.2, −83.5, −84.4 to −87.2, −89.1 to −90.7, −130.2, −145.5.

Ex. 13-2

In the same manner as in (Ex. 3) except that instead of compound (α2-1), 1.10 g of compound (α7-1) was used, a mixture comprising compound (14-11c) wherein one of G$^1$ to G$^3$ in the formula (13) is a group represented by the following formula (14c), and the rest are groups represented by the following formula (15); a compound wherein two of G$^1$ to G$^3$ are groups represented by the following formula (14c), and the rest is a group represented by the following formula (15); a compound wherein all of G$^1$ to G$^3$ are groups represented by the following formula (14c); and a compound wherein all of G$^1$ to G$^3$ are groups represented by the following formula (15), was obtained. As the mixture, the number average molecular weight (Mn) was 2,400, and the proportion of fluorine atoms was 23 mass %.

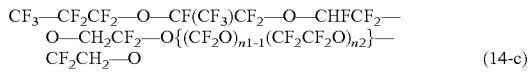
(14-c)

Average value of the number of units n1−1: 8.
Average value of the number of units n2: 10.

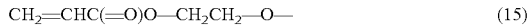
(15)

NMR Spectra of Compound (14-11c):
$^1$H-NMR (300.4 MHz, solvent: deuterated chloroform+ R-113, standard: TMS) δ (ppm): 1.19 to 1.76, 3.19, 3.29, 3.74, 3.88, 4.30, 4.85 to 5.28, 5.84, 6.15, 6.45.
$^{19}$F-NMR (282.7 MHz, solvent: deuterated chloroform+ R-113, standard: CFCl$_3$) δ (ppm): −52.4 to −55.8, −78.5, −80.6, −82.2, −84.4 to −87.2, −89.1 to −90.7, −130.2, −145.5.

[Ex. 14] Example for Forming Hard Coat Layer

A hard coat layer-forming composition (7) and a hard coat layer were obtained in the same manner as in Ex. 3 except that instead of compound (14-11a), compound (14-11c) obtained in Ex. 13 was used.

The composition of the hard coat layer-forming composition (7), and the evaluation results of the hard coat layer, are shown in Table 2.

[Ex. 15] Example for Producing Compound (14-11d)

Ex. 15-1

Compound (α8-1) was synthesized in accordance with the method disclosed in WO2004/035656.

(α8-1)

Average value of the number of units n3: 10.

Ex. 15-2

Compound (α8-2) (yield: 40.1%) was obtained in the same manner as in (Ex. 1-1) except that instead of compound (α1), compound (α8-1) was used.

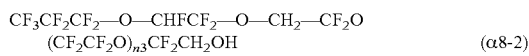

(α8-2)

Average value of the number of units n3: 10.

NMR Spectra of Compound (α6-1):
$^1$H-NMR (300.4 MHz, solvent: deuterated chloroform, standard: TMS) δ (ppm): 3.9, 4.2, 5.8 to 6.0.
$^{19}$F-NMR (282.7 MHz, solvent: deuterated chloroform, standard: CFCl$_3$) δ (ppm): −55.7, −78.8, −80.8, −81.4, −82.2, −83.5, −85.3 to −88.2, −89.4 to −91.1, −130.5, −145.1.

Ex. 15-2

In the same manner as in (Ex. 3) except that instead of compound (α2-1), 0.69 g of compound (α8-2) was used, a mixture comprising compound (14-11d) wherein one of G$^1$ to G$^3$ in the formula (13) is a group represented by the following formula (14d), and the rest are groups represented by the following formula (15); a compound wherein two of G$^1$ to G$^3$ are groups represented by the following formula (14d), and the rest is a group represented by the following formula (15); a compound wherein all of G$^1$ to G$^3$ are groups represented by the following formula (14d); and a compound wherein all of G$^1$ to G$^3$ are groups represented by the following formula (15), was obtained. As the mixture, the number average molecular weight (Mn) was 1,600, and the proportion of fluorine atoms was 17 mass %.

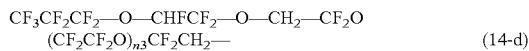

(14-d)

Average value of the number of units n3: 10.

$$CH_2=CHC(=O)O-CH_2CH_2-O-$$ (15)

NMR Spectra of Compound (14-11d):
$^1$H-NMR (300.4 MHz, solvent: deuterated chloroform+ R-113, standard: TMS) δ (ppm): 1.19 to 1.76, 3.19, 3.29, 3.74, 3.88, 4.30, 4.85 to 5.28, 5.84, 6.15, 6.45.
$^{19}$F-NMR (282.7 MHz, solvent: deuterated chloroform+ R-113, standard: CFCl$_3$) δ (ppm): −55.7, −78.5, −80.6, −82.2, −86.8, −89.4, −91.0, −130.6, −145.0.

[Ex. 16] Example for Forming Hard Coat Layer

A hard coat layer-forming composition (8) and a hard coat layer were obtained in the same manner as in Ex. 3 except that instead of compound (14-11a), compound (14-11d) obtained in Ex. 15 was used.

The composition of the hard coat layer-forming composition (8), and the evaluation results of the hard coat layer, are shown in Table 2.

[Ex. 17] Example for Producing Compound (16-11a)

In the same manner as in (Ex. 3) except that instead of isocyanurate-modified hexamethylene diisocyanate, 1.25 g of burette-modified hexamethylene diisocyanate (trimer of hexamethylene diisocyanate, manufactured by Asahi Kasei Chemicals Corporation, tradename: DURANATE P301-70) was used, a mixture comprising compound (16-11a) wherein one of G$^1$ to G$^3$ in the formula (16) is a group represented by the formula (14a), and the rest are groups represented by the formula (15); a compound wherein two of G$^1$ to G$^3$ are groups represented by the formula (14d), and the rest is a group represented by the formula (15); a compound wherein all of G$^1$ to G$^3$ are groups represented by the formula (14a); and a compound wherein all of G$^1$ to G$^3$ are groups represented by the formula (15), was obtained. As the mixture, the number average molecular weight (Mn) was 2,000, and the proportion of fluorine atoms was 24 mass %.

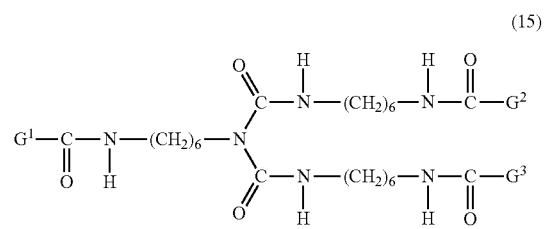

(15)

NMR Spectra of Compound (15-11a):
$^1$H-NMR (300.4 MHz, solvent: deuterated chloroform+ R-113, standard: TMS) δ (ppm): 1.19 to 1.76, 3.18 to 3.89, 4.30, 4.85 to 5.28, 5.84, 6.15, 6.45.
$^{19}$F-NMR (282.7 MHz, solvent: deuterated chloroform+ R-113, standard: CFCl$_3$) δ (ppm): −55.7, −78.5, −80.6, −82.2, −86.8, −89.4, −91.0, −130.6, −145.0.
3.9, 4.2, 5.9

[Ex. 18] Example for Forming Hard Coat Layer

A hard coat layer-forming composition (9) and a hard coat layer were obtained in the same manner as in Ex. 3 except that instead of compound (14-11a), compound (16-11a) obtained in Ex. 17 was used.

The composition of the hard coat layer-forming composition (9), and the evaluation results of the hard coat layer, are shown in Table 2.

[Ex. 19] Example for Producing Compound (C)

In accordance with the method as described in Ex. 3, a mixture comprising compound (C) wherein one of G$^1$ to G$^3$ in the formula (13) is a group represented by the following formula (14-2), and the rest are groups represented by the formula (15); a compound wherein two of G$^1$ to G$^3$ are groups represented by the following formula (14-2), and the rest is a group represented by the formula (15); a compound wherein all of G$^1$ to G$^3$ are groups represented by the following formula (14-2); and a compound wherein all of G$^1$ to G$^3$ are groups represented by the formula (15), was obtained. As the mixture, the number average molecular weight (Mn) was 1,400, and the proportion of fluorine atoms was 29 mass %.

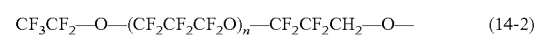

(14-2)

[Ex. 20] Example for Forming Hard Coat Layer

A hard coat layer-forming composition (10) and a hard coat layer were obtained in the same manner as in Ex. 3 except that instead of compound (14-11a), compound (C) obtained in Ex. 19 was used.

The composition of the hard coat layer-forming composition (10), and the evaluation results of the hard coat layer, are shown in Table 2.

TABLE 1

| | Ex. | | 2 | 4 | 6 | 8 | 10 |
|---|---|---|---|---|---|---|---|
| | Fluorinated compound or polymer | | Compound (111-1) | Compound (14-11a) | Polymer (A) | Compound (B) | Compound (14-11b) |
| | Number average molecular weight | | 2,200 | 1,400 | 2,400 | 1,800 | 4,800 |
| | Hard coat layer-forming composition | | Composition (1) | Composition (2) | Composition (3) | Composition (4) | Composition (5) |
| | Proportion [mass %] in solid content (100 mass %) | Fluorinated compound or polymer | 1 | 0.5 | 1 | 0.1 | 1 |
| | | Photopoly- merizable compound (a-1) | 46.6 | 47 | 46.6 | 47 | 46.6 |
| | | (a-2) | 46.6 | 47 | 46.6 | 47 | 46.6 |
| | | Photopoly- merization initiator (b-1) | 5.8 | 5.5 | 5.8 | 5.9 | 5.8 |
| | Proportion [mass %] in composition (100 mass %) | Organic solvent (c-1) | — | 5.4 | — | — | — |
| | | (c-2) | 5.3 | — | — | — | 5.3 |
| | | (c-3) | — | — | — | 5.4 | — |
| | | (c-4) | 34.7 | 34.9 | 40 | 34.9 | 34.7 |
| Evaluation results | Water contact angle [degrees] | | 100.5 | 102.5 | 98 | 102 | 105.1 |
| | Oleic acid contact angle [degrees] | | 67 | 68.8 | 54.3 | 67 | 69 |
| | Compatibility | | ○ | ○ | x | ○ | ○ |
| | Storage stability | | ○ | ○ | x | x | ○ |
| | Appearance of hard coat layer | | ○ | ○ | ○ | ○ | ○ |
| | Oily ink repellency | | ○ | ○ | Δ | Δ | ○ |
| | Fingerprint stain removability | | ○ | ○ | Δ | ○ | ○ |
| | Pencil hardness | | 2H | 2H | 2H | 2H | 2H |
| | Abrasion resistance | Water contact angle [degrees] | 91 | 92.3 | 75.1 | 80.1 | 93 |
| | | Oleic acid contact angle [degrees] | 65.1 | 65.1 | 45.8 | 64.1 | 65.2 |
| | Dynamic friction coefficient | | 0.4 | 0.35 | 1.25 | 0.58 | 0.33 |

TABLE 2

| | Ex. | | 12 | 14 | 16 | 18 | 20 |
|---|---|---|---|---|---|---|---|
| | Fluorinated compound or polymer | | Compound (14-12b) | Compound (14-11c) | Compound (14-11d) | Compound (16-11a) | Compound (C) |
| | Number average molecular weight | | 4,900 | 2,400 | 1,600 | 2,000 | 1,400 |
| | Hard coat layer-forming composition | | Composition (6) | Composition (7) | Composition (8) | Composition (9) | Composition (10) |
| | Proportion [mass %] in solid content (100 mass %) | Fluorinated compound or polymer | 1 | 1 | 1 | 1 | 1 |
| | | Photopoly- merizable compound (a-1) | 46.6 | 46.6 | 46.6 | 46.6 | 46.6 |
| | | (a-2) | 46.6 | 46.6 | 46.6 | 46.6 | 46.6 |
| | | Photopoly- merization initiator (b-1) | 5.8 | 5.8 | 5.8 | 5.8 | 5.8 |
| | Proportion [mass %] in composition (100 mass %) | Organic solvent (c-1) | — | — | — | — | — |
| | | (c-2) | 5.3 | 5.3 | 5.3 | 5.3 | 5.3 |
| | | (c-3) | — | — | — | — | — |
| | | (c-4) | 34.7 | 34.7 | 34.7 | 34.7 | 34.7 |
| Evaluation results | Water contact angle [degrees] | | 104.8 | 103.3 | 100.3 | 101.9 | 104 |
| | Oleic acid contact angle [degrees] | | 67.5 | 69.8 | 67 | 68 | 69 |
| | Compatibility | | ○ | ○ | ○ | ○ | ○ |
| | Storage stability | | ○ | ○ | ○ | ○ | x |
| | Appearance of hard coat layer | | ○ | ○ | ○ | ○ | Δ |
| | Oily ink repellency | | ○ | ○ | ○ | ○ | ○ |
| | Fingerprint stain removability | | ○ | ○ | ○ | ○ | ○ |
| | Pencil hardness | | 2H | 2H | 2H | 2H | 2H |
| | Abrasion resistance | Water contact angle [degrees] | 95 | 93.3 | 90 | 89 | 80.8 |
| | | Oleic acid contact angle [degrees] | 65.5 | 66.1 | 65.1 | 65.1 | 59 |
| | Dynamic friction coefficient | | 0.39 | 0.34 | 0.4 | 0.39 | 0.5 |

The hard coat layer in Ex. 2 formed by using compound (111-1), the hard coat layer in Ex. 4 formed by using compound (14-11a), the hard coat layer in Ex. 10 formed by using compound (14-11b), the hard coat layer in Ex. 12 formed by using compound (14-12b), the hard coat layer in Ex. 14 formed by using compound (14-11c), the hard coat layer in Ex. 16 formed by using compound (14-11d), and the hard coat layer in Ex. 18 formed by using compound (16-11a), were excellent in antifouling properties (oily ink repellency, fingerprint stain removability) and high in the water contact angle and oleic acid contact angle serving as indices of antifouling properties. Further, the hard coat layer-forming compositions in Ex. 2, 4, 10, 12, 14, 16 and 18 were excellent in compatibility and storage stability. Further, the hard coat layers in Ex. 2, 4, 10, 12, 14, 16 and 18 were excellent in lubricity with small dynamic friction coefficient and at the same time, excellent also in appearance and abrasion resistance.

Whereas, the hard coat layer in Ex. 6 formed by using a conventional fluorinated polymer was low in the water contact angle and oleic acid contact angle, and inadequate in antifouling properties. Further, the dynamic friction coefficient was also very high. The compatibility of the polymer and the storage stability of the hard coat layer-forming composition in Ex. 6 were inadequate. Further, the hard coat layer in Ex. 8 formed by using a conventional compound had a large dynamic friction coefficient and was inadequate in lubricity. The storage stability of the hard coat layer-forming composition in Ex. 8 was inadequate. The hard coat layer in Ex. 20 was inadequate in abrasion resistance, although the water contact angle and oleic acid contact angle were high. The storage stability of the hard coat layer-forming composition in Ex. 20 was inadequate.

INDUSTRIAL APPLICABILITY

The fluorinated compound of the present invention is useful for imparting excellent antifouling properties (oily ink repellency, fingerprint stain removability) and lubricity to an object (such as a hard coat layer). Further, it is useful as mixed with a resin material, for an application to impart antifouling properties (oily ink repellency, fingerprint stain removability) to a molded product, as a mold release agent, for prevention of oil leakage from e.g. bearings, for prevention of adhesion of a process solution at the time of processing e.g. electronic components, for moisture prevention for processed products, etc.

What is claimed is:

1. A fluorinated compound represented by the formula (1):

  (1)

wherein $D^1$ is $CF_3$— or $CF_3$—O—, $R^{11}$ is a $C_{1-20}$ fluoroalkylene group containing at least one hydrogen atom, a $C_{2-20}$ fluoroalkylene group containing at least one hydrogen atom and having an etheric oxygen atom between carbon-carbon atoms, a $C_{1-20}$ alkylene group, or a $C_{2-20}$ alkylene group having an etheric oxygen atom between carbon-carbon atoms, m is an integer of from 1 to 6, n is an integer of from 1 to 200, provided that when n is at least 2, $(C_mF_{2m}O)_n$ optionally has at least 2 types of $C_mF_{2m}O$ different in m, and A is a monovalent organic group having at least one —C(=O)—$CR^1$=$CH_2$ where $R^1$ is a hydrogen atom or a methyl group, wherein A in the formula (1) is represented by the formula (A2):

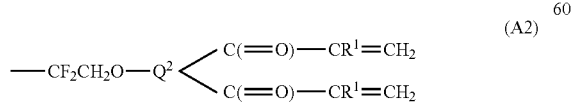  (A2)

wherein $Q^2$ has any of groups represented by the following formulae (7-1) to (7-3):

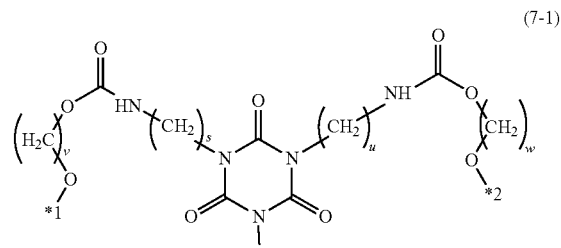  (7-1)

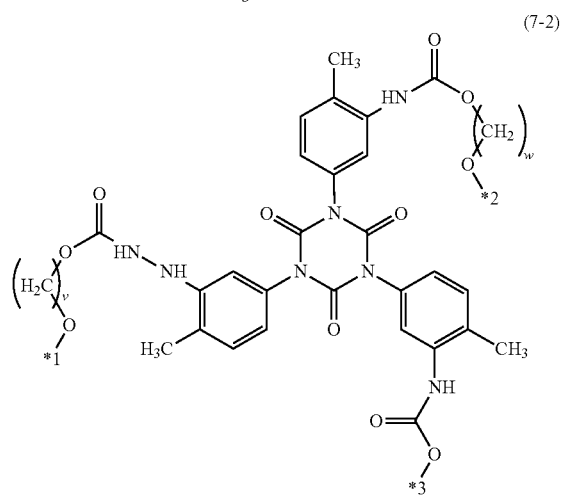  (7-2)

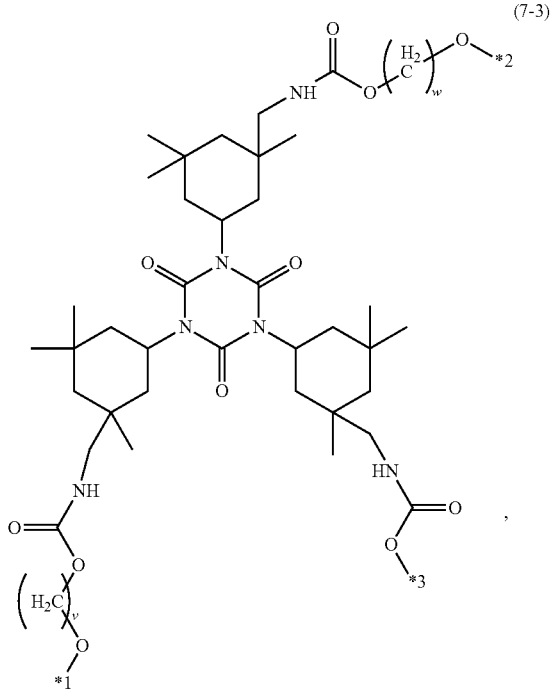  (7-3)

wherein each of s, t, u, v and w which are independent of one another, is an integer of from 2 to 10, each of *1 and *2 is bonded to —C(=O)—$CR^1$=$CH_2$ in the above formula (A2), and *3 is bonded to $(C_mF_{2m}O)_n$ in the above formula (1) via —$CH_2CF_2$— or a bivalent organic group having —$CH_2CF_2$— at its one terminal.

2. The fluorinated compound according to claim 1, wherein the $(C_mF_{2m}O)_n$ is $\{(CF_2O)_{n1}(CF_2CF_2O)_{n2}\}$ where n1 is an integer of at least 1, and n2 is an integer of at least 0, provided that n1+n2 is an integer of from 1 to 200, and bonding order of n1 number of $CF_2O$ and n2 number of $CF_2CF_2O$ is not limited.

3. The fluorinated compound according to claim 1, wherein the $R^{f1}$ is a group represented by the formula (2-1), a group represented by the formula (2-2), or a group represented by the formula (2-3):

$$—R^F—O—CHFCF_2— \quad (2\text{-}1)$$

$$—R^F—CHFCF_2— \quad (2\text{-}2)$$

$$—R^F—C_zH_{2z} \quad (2\text{-}3)$$

wherein $R^F$ is a single bond, a $C_{1-15}$ perfluoroalkylene group, or a $C_{2-15}$ perfluoroalkylene group having an etheric oxygen atom between carbon-carbon atoms, and z is an integer of from 1 to 4.

4. The fluorinated compound according to claim 1, which has a number average molecular weight of from 800 to 80,000.

5. A hard coat layer-forming composition, comprising:
the fluorinated compound of claim 1;
a photopolymerizable compound other than the fluorinated compound; and
a photopolymerization initiator.

6. The hard coat layer-forming composition according to claim 5, further comprising:
a liquid medium.

7. The hard coat layer-forming composition according to claim 6, wherein the fluorinated compound is included in an amount of from 0.01 to 5 mass % in 100 mass % of a solid content.

8. An article, comprising:
a substrate; and
a hard coat layer formed from the hard coat layer-forming composition of claim 5.

9. The article according to claim 8, wherein the substrate is made of a metal, a resin, a glass, a ceramics, or a composite material thereof.

10. The fluorinated compound according to claim 1, which has a number average molecular weight of from 1,000 to 40,000.

11. The fluorinated compound according to claim 1, which has a number average molecular weight of from 1,200 to 30,000.

12. The fluorinated compound according to claim 1, having fluorine atoms in an amount of from 0.1 to 80 mass %.

13. The fluorinated compound according to claim 1, having fluorine atoms in an amount of from 5 to 65 mass %.

* * * * *